(12) United States Patent
Frankel et al.

(10) Patent No.: US 10,117,564 B2
(45) Date of Patent: Nov. 6, 2018

(54) ULTRASOUND AND DETACHABLE INSTRUMENT FOR PROCEDURES

(71) Applicant: Hitachi Aloka Medical, Inc., Tokyo (JP)

(72) Inventors: Bruce M. Frankel, Charleston, SC (US); Randall R. Baraso, Mount Pleasant, SC (US); Thomas P. Oko, Shelton, CT (US)

(73) Assignee: Hitachi Healthcare Americas Corporation, Twinsburg, OH (US)

( * ) Notice: Subject to any disclaimer, the term of this patent is extended or adjusted under 35 U.S.C. 154(b) by 277 days.

(21) Appl. No.: 14/701,642

(22) Filed: May 1, 2015

(65) Prior Publication Data

US 2015/0230690 A1    Aug. 20, 2015

Related U.S. Application Data

(63) Continuation-in-part of application No. 13/087,648, filed on Apr. 15, 2011.
(Continued)

(51) Int. Cl.
*A61B 8/14* (2006.01)
*A61B 1/00* (2006.01)
(Continued)

(52) U.S. Cl.
CPC ........ *A61B 1/00087* (2013.01); *A61B 1/3132* (2013.01); *A61B 8/0808* (2013.01);
(Continued)

(58) Field of Classification Search
CPC . A61B 17/295; A61B 1/00087; A61B 1/3132; A61B 2017/00106;
(Continued)

(56) References Cited

U.S. PATENT DOCUMENTS 3,938,502 A    2/1976    Bom
3,942,530 A    3/1976    Northeved
(Continued)

FOREIGN PATENT DOCUMENTS

DE    102005047527    4/2007
WO    WO 1995/019143    7/1995
WO    WO 2007/039036    4/2007

OTHER PUBLICATIONS

Maguire et al., Evaluation of Intrapedicular Screw Position Using Intraoperative Evoked Electromyography, Spine, 20(9), p. 1068-1074, 1995.
(Continued)

*Primary Examiner* — Mark Remaly
(74) *Attorney, Agent, or Firm* — McCarter & English, LLP

(57) ABSTRACT

The present disclosure relates generally to equipment and procedures in the field of surgery and/or diagnostics and, more particularly, to instruments, assemblies and methods for undertaking surgical and/or diagnostic procedures that involve and/or are in proximity to the brain (e.g., cranial procedures and/or surgery). The disclosed assemblies generally include a handle member and an elongated probe that includes an ultrasound transducer. The assemblies may be used in conjunction with K-wires/guidewires, tubular members (e.g., EVD catheters and/or ventricular drains), endoscopes/cameras, and accessory items such as curettes, probes, knives, suction devices, scissors, cautery units, forceps, grasping devices and the like. Advantageous medical diagnostic and surgical instruments, assemblies and methods are provided for use during a broad variety of clinical applications and procedures (e.g., procedures within the cranium and/or in connection with or in proximity to the brain, spinal surgical procedures, orthopedic applications, minimally invasive surgical procedures, etc.).

20 Claims, 17 Drawing Sheets

Related U.S. Application Data

(60) Provisional application No. 61/324,845, filed on Apr. 16, 2010.

(51) Int. Cl.

| | | |
|---|---|---|
| *A61B 8/12* | (2006.01) | |
| *A61B 8/00* | (2006.01) | |
| *A61B 17/295* | (2006.01) | |
| *A61B 8/08* | (2006.01) | |
| *A61M 25/09* | (2006.01) | |
| *A61B 1/313* | (2006.01) | |
| *A61B 17/00* | (2006.01) | |
| *A61M 25/01* | (2006.01) | |

(52) U.S. Cl.
CPC .............. *A61B 8/0841* (2013.01); *A61B 8/12* (2013.01); *A61B 8/445* (2013.01); *A61B 8/4494* (2013.01); *A61B 17/295* (2013.01); *A61M 25/09* (2013.01); *A61B 2017/00106* (2013.01); *A61B 2017/00296* (2013.01); *A61B 2217/005* (2013.01); *A61M 2025/0177* (2013.01)

(58) Field of Classification Search
CPC .... A61B 2017/00296; A61B 2217/005; A61B 8/0808; A61B 8/0841; A61B 8/12; A61B 8/445; A61B 8/4494; A61M 2025/0177; A61M 25/09
See application file for complete search history.

(56) References Cited

U.S. PATENT DOCUMENTS

| | | | |
|---|---|---|---|
| 4,273,111 A | 6/1981 | Tsukaya | |
| 4,462,408 A | 7/1984 | Silverstein et al. | |
| 4,489,727 A | 12/1984 | Matsuo et al. | |
| 4,582,067 A | 4/1986 | Silverstein et al. | |
| 4,756,313 A | 7/1988 | Terwilliger | |
| 4,951,677 A | 8/1990 | Crowley et al. | |
| 5,070,879 A | 10/1991 | Herres | |
| 5,088,500 A | 2/1992 | Wedel et al. | |
| 5,090,414 A | 2/1992 | Takano | |
| 5,154,723 A | 10/1992 | Kubota et al. | |
| 5,196,015 A | 3/1993 | Neubardt | |
| 5,275,166 A | 1/1994 | Vaitekunas et al. | |
| 5,325,860 A | 7/1994 | Seward et al. | |
| 5,345,940 A | 9/1994 | Seward et al. | |
| 5,372,138 A | 12/1994 | Crowley et al. | |
| 5,413,107 A | 5/1995 | Oakley et al. | |
| 5,421,338 A | 6/1995 | Crowley et al. | |
| 5,429,136 A | 7/1995 | Milo et al. | |
| 5,474,558 A | 12/1995 | Neubardt | |
| 5,499,630 A | 3/1996 | Hiki et al. | |
| 5,512,034 A | 4/1996 | Finn et al. | |
| 5,524,630 A | 6/1996 | Crowley | |
| 5,588,432 A | 12/1996 | Crowley | |
| 5,680,863 A | 10/1997 | Hossack et al. | |
| 5,697,897 A | 12/1997 | Buchholtz et al. | |
| 5,704,361 A | 1/1998 | Seward et al. | |
| 5,713,363 A | 2/1998 | Seward et al. | |
| 5,715,825 A | 2/1998 | Crowley | |
| 5,735,792 A | 4/1998 | Vanden Hoek et al. | |
| 5,752,517 A | 5/1998 | Harman et al. | |
| 5,840,031 A | 11/1998 | Crowley | |
| 5,846,204 A | 12/1998 | Solomon | |
| 5,846,205 A | 12/1998 | Curley et al. | |
| 6,004,269 A | 12/1999 | Crowley et al. | |
| 6,036,649 A | 3/2000 | Yuasa | |
| 6,039,693 A | 3/2000 | Seward et al. | |
| 6,045,508 A | 4/2000 | Hossack et al. | |
| 6,059,731 A | 5/2000 | Seward et al. | |
| 6,099,475 A | 8/2000 | Seward et al. | |
| 6,109,270 A | 8/2000 | Mah et al. | |
| 6,129,672 A | 10/2000 | Seward | |
| 6,149,599 A | 11/2000 | Schlesinger et al. | |
| 6,165,127 A | 12/2000 | Crowley | |
| 6,171,247 B1 | 1/2001 | Seward | |
| 6,190,353 B1 | 2/2001 | Makower et al. | |
| 6,224,552 B1 | 5/2001 | Jago et al. | |
| 6,241,667 B1 | 6/2001 | Vetter et al. | |
| 6,299,580 B1 | 10/2001 | Asafusa | |
| 6,302,875 B1 | 10/2001 | Makower et al. | |
| 6,306,096 B1 | 10/2001 | Seward | |
| 6,306,097 B1 | 10/2001 | Park et al. | |
| 6,364,840 B1 | 4/2002 | Crowley | |
| 6,398,736 B1 | 6/2002 | Seward | |
| 6,413,215 B1 | 7/2002 | Wu et al. | |
| 6,432,058 B1 | 8/2002 | Sloth | |
| 6,438,413 B1 | 8/2002 | Taheri | |
| 6,464,645 B1 | 10/2002 | Park et al. | |
| 6,544,187 B2 | 4/2003 | Seward | |
| 6,556,695 B1 | 4/2003 | Packer et al. | |
| 6,572,553 B2 | 6/2003 | Crowley | |
| 6,579,244 B2 | 6/2003 | Goodwin | |
| 6,585,651 B2 | 7/2003 | Nolte et al. | |
| 6,585,655 B2 | 7/2003 | Crowley | |
| 6,592,520 B1 | 7/2003 | Peszynski et al. | |
| 6,655,386 B1 | 12/2003 | Makower et al. | |
| 6,656,136 B1 | 12/2003 | Weng et al. | |
| 6,719,692 B2 | 4/2004 | Kleffner et al. | |
| 6,746,402 B2 | 6/2004 | Ustuner | |
| 6,796,985 B2 | 9/2004 | Bolger et al. | |
| 6,849,047 B2 | 2/2005 | Goodwin | |
| 6,855,105 B2 | 2/2005 | Jackson | |
| 6,978,171 B2 | 12/2005 | Goetz et al. | |
| 7,037,271 B2 | 5/2006 | Crowley | |
| 7,059,330 B1 | 6/2006 | Makower et al. | |
| 7,134,438 B2 | 11/2006 | Makower et al. | |
| 7,156,812 B2 | 1/2007 | Seward et al. | |
| 7,211,055 B2 | 5/2007 | Diederich | |
| 7,258,668 B2 | 8/2007 | Hirooka et al. | |
| 7,270,658 B2 | 9/2007 | Woloszko et al. | |
| 7,297,115 B2 | 11/2007 | Bates et al. | |
| 7,493,703 B2 | 2/2009 | Kim et al. | |
| 7,503,895 B2 | 3/2009 | Rabiner et al. | |
| 7,699,782 B2 | 4/2010 | Angelsen et al. | |
| 7,776,003 B2 | 8/2010 | Zauner | |
| 7,815,571 B2 | 10/2010 | Gerbi et al. | |
| 7,819,826 B2 | 10/2010 | Diederich et al. | |
| 8,007,440 B2 | 8/2011 | Magnin et al. | |
| 8,206,306 B2 | 6/2012 | Baraso et al. | |
| 8,298,146 B2 | 10/2012 | Amara et al. | |
| 8,343,056 B2 | 1/2013 | Baraso et al. | |
| 8,386,018 B2 | 2/2013 | Stauch et al. | |
| 2001/0031924 A1 | 10/2001 | Seward | |
| 2003/0205029 A1 | 11/2003 | Chapolini et al. | |
| 2004/0039372 A1 | 2/2004 | Carmody | |
| 2005/0101866 A1 | 5/2005 | Goodwin | |
| 2005/0182324 A1 | 8/2005 | Angelsen et al. | |
| 2005/0203416 A1 | 9/2005 | Angelsen et al. | |
| 2005/0272975 A1 | 12/2005 | McWeeney et al. | |
| 2006/0178594 A1 | 8/2006 | Neubardt et al. | |
| 2006/0235299 A1 | 10/2006 | Martinelli | |
| 2006/0276721 A1 | 12/2006 | McGinnis | |
| 2007/0167821 A1 | 7/2007 | Lee et al. | |
| 2007/0167823 A1 | 7/2007 | Lee et al. | |
| 2008/0228231 A1 | 9/2008 | Raphael et al. | |
| 2009/0099605 A1 | 4/2009 | Wade et al. | |
| 2009/0105597 A1 | 4/2009 | Abraham | |
| 2011/0009739 A1 | 1/2011 | Philips | |

OTHER PUBLICATIONS

Yongjung, Kim J. et al., Thoracic pedicle screw placement: Freehand technique, Neurology India, vol. 53, No. 4, p. 512-510, 2005.

Kantelhardt, Sven R. et al., Intraosseous Ultrasound in the Placement of Pedicle Screws in the Lumbar Spine, Spine, vol. 34, No. 4, p. 400-407, 2009.

Kantelhardt, Sven R. et al., Intra-osseous ultrasound for pedicle screw positioning in the subaxial cervical spine: an experimental study, Acta Neurochir, DOI 10.1007/s00701-009-0447-6, 2009.

(56) References Cited

OTHER PUBLICATIONS

The Laguna Pedicle Screw System Surgical Technique Guide, Pedicle Preparation, Allez Spine, Doc. 56003_B, p. 9, 2009, available at http://www.allerspine.com/pdfs/56003_C_Laguna_Surgical_Technique_Guide.pdf.

Minimally Invasive Spine Surgery, Taiwan Spine Center, 2009, available at http://www.taiwanspinecenter.com/tsc_e/sur_treatment/minimally_invasive.htm.

Pedicle Screw Stimulator, Consolidated Neuro Supply, 2009, available at http://www.neurosupply.com/subdermal_needles.htm.

Spine Navigation Software, Stryker, 2009, available at http://www.stryker.com/en-us/products/Spine/SpineNavigationSurgery/index.htm.

Smart Instrumentation for Spine Navigation Surgery, Stryker, 2009, available at http://www.stryker.com/en-us/products/Spine/SpineNavigationSurgery/006198.

Spinal Navigation & 3-D Imaging: Giving Doctors and Patients the Whole Picture, Sky Ridge Medical Center, p. 18-19, 2009, available at http://www.skyridge.ehc.com/CPM/Health%20and%20Wellness%20Spine%20Choi%2Oreduced.pdf.

Peterson, Devin, Idiopathic Scoliosis, McMaster University, 2010, available at fhs.mcmaster.ca/surgery/documents/idiopathic_scoliosis.pdf.

PCT International Search Report and Written Opinion for WO 2010/129773 dated Jul. 19, 2010.

PCT International Search Report and Written Opinion for PCT/2011/058074 dated Feb. 8, 2012.

U.S. Appl. No. 13/087,648, filed Apr. 15, 2011, 2011/0313282.

U.S. Appl. No. 61/324,845, filed Apr. 16, 2011.

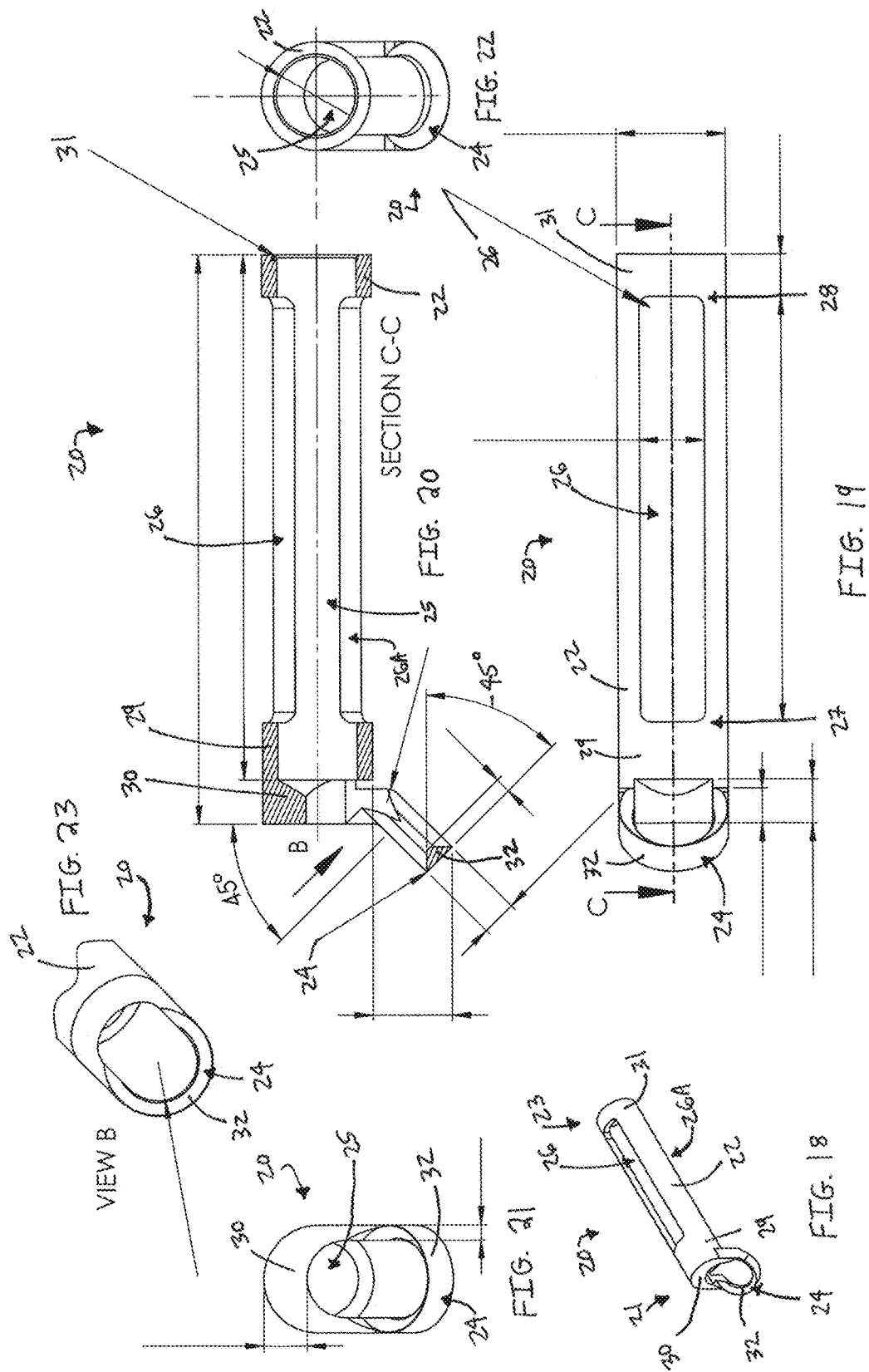

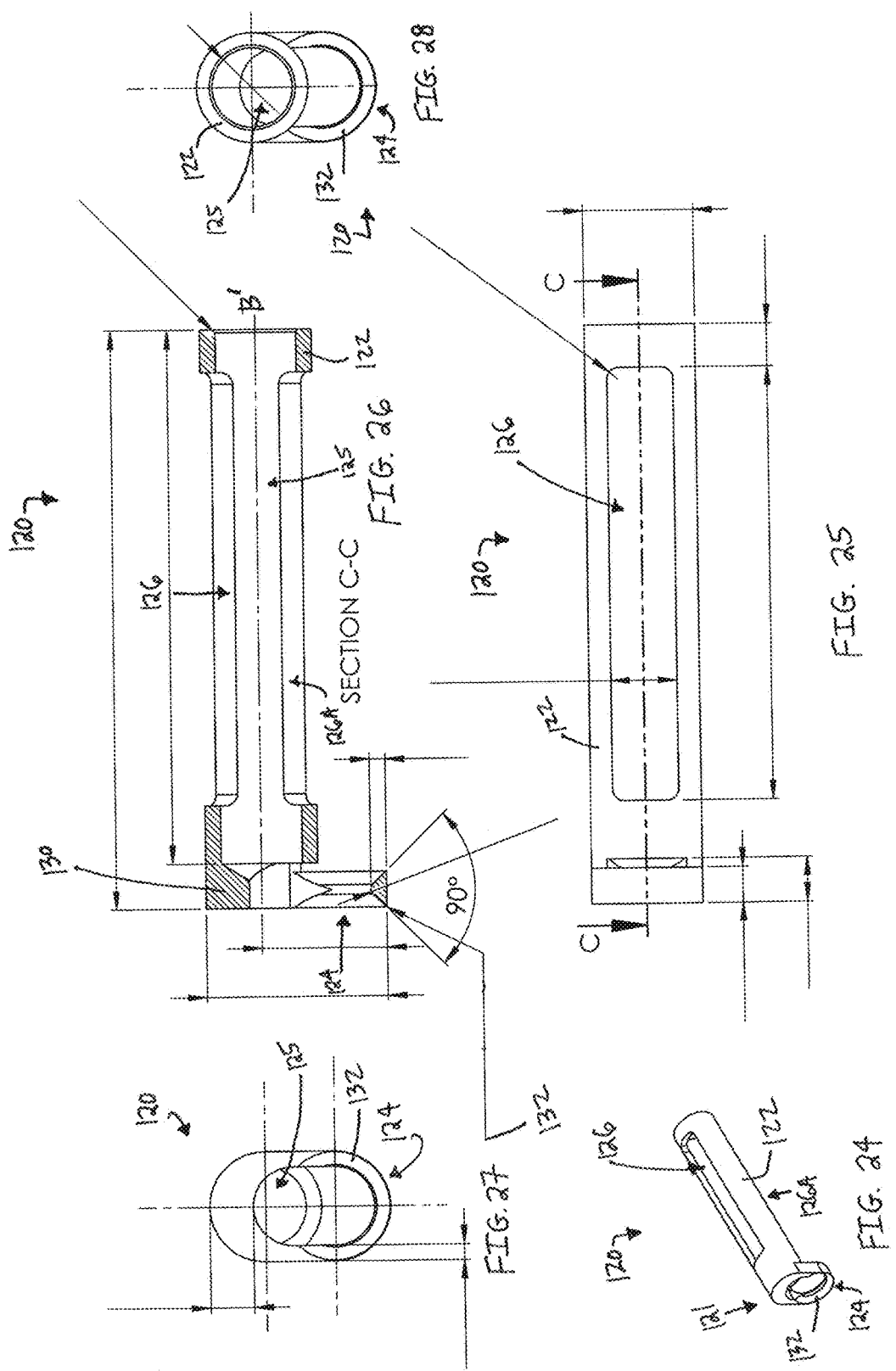

ULTRASOUND AND DETACHABLE INSTRUMENT FOR PROCEDURES

CROSS-REFERENCE TO RELATED APPLICATIONS

This application claims priority to and is a continuation-in-part of co-pending U.S. patent application Ser. No. 13/087,648 (entitled "ULTRASOUND FOR SURGICAL CRANIAL APPLICATIONS") filed Apr. 15, 2011, which claims priority to Provisional App. Ser. No. 61/324,845 filed Apr. 16, 2010, both of which are hereby incorporated by reference in their entireties.

FIELD OF THE DISCLOSURE

The present disclosure relates generally to equipment and procedures in the field of surgery and/or diagnostics and, more particularly, to instruments, assemblies and methods for undertaking surgical and/or diagnostic procedures that involve and/or are in proximity to the brain (e.g., cranial applications).

BACKGROUND OF THE DISCLOSURE

Recent developments in the use of ultrasound technology in surgical applications have shown promise. With the increasing miniaturization of electronics generally has come the ability to position ultrasound transducers to beneficial effect in increasingly smaller and, at least up until recently, harder to reach anatomical locations.

In general, surgical and diagnostic procedures (e.g., procedures that are in proximity to the brain, spinal surgical procedures, minimally invasive surgical procedures, etc.) require significant care to minimize the risk of inadvertent damage/injury to surrounding anatomical structures.

For example, in pituitary surgical procedures, it is important to minimize the risk of injury to surrounding anatomical structures (e.g., the cavernous sinus contents). Surgical experience is valuable in reducing the risk of inadvertent injury. In addition, visualization techniques that employ microscopic, endoscopic and/or neuro-navigational equipment have been used to reduce injury risk.

However, despite prior efforts to reduce injury risk in such surgical/diagnostic procedures, a need remains for improved instruments, assemblies and methods that facilitate desired surgical and/or diagnostic objectives, while minimizing the risk of injury to surrounding structures. In addition, a need remains for instruments, assemblies and methods that fulfill the noted objectives through designs and techniques that are easily understood and implemented by surgical personnel.

These and other needs are satisfied by the instruments, assemblies and methods disclosed herein, as will be apparent from the detailed description which follows, particularly when read in conjunction with the figures appended hereto.

SUMMARY OF THE DISCLOSURE

According to the present disclosure, advantageous instruments, assemblies and methods are provided for undertaking surgical and/or diagnostic procedures (e.g., cranial procedures/applications that are in proximity to the brain, spinal surgical procedures, orthopedic applications, minimally invasive surgical procedures, etc.).

In an exemplary embodiment, the disclosed instrument, assembly and method generally includes a handle member that defines a guide wire channel and an elongated probe that is adapted to mount with respect to (or otherwise cooperate with) the handle member. The elongated probe includes an ultrasound transducer positioned at or near a distal end thereof. In some embodiments, the ultrasound transducer is directed in a perpendicular or substantially perpendicular orientation relative to the axis of the elongated probe, such that non-axial ultrasound imaging is facilitated. In alternative implementations, the ultrasound transducer is directed in an axial or substantially axial orientation relative to the axis of the elongated probe. The handle member of the disclosed instruments/assemblies generally cooperates with conventional cabling for communication to and with the elongated probe and, in particular, the distally-positioned ultrasound transducer.

In use, the handle member of the disclosed instrument/assembly is adapted to receive a K-wire (or other guidewire) through the guide channel defined therein. The K-wire/guidewire may take various forms and exhibit various characteristics. For example, the K-wire/guidewire may be substantially rigid or flexible and may include a sharp or blunt end. In addition, exemplary implementations of the present disclosure may include a K-wire/guidewire that is threaded, in whole or in part. The K-wire/guidewire generally extends axially alongside the elongated probe such that its distal end may be positioned in close proximity to the region under ultrasound imaging. Thus, in exemplary embodiments, the handle is configured and dimensioned such that a stepped geometry is defined. The guide channel is formed in the outwardly stepped region of the handle, such that a K-wire that passes through the guide channel can easily run alongside the elongated probe in a substantially linear fashion.

The elongated probe with associated K-wire/guidewire may be advantageously introduced to a desired anatomical region (e.g., into the cranium of a patient) with real-time ultrasound imaging of anatomical structures adjacent thereto. In this way, potential injuries associated with inadvertent contact of the K-wire/guidewire with adjacent anatomical structures/features may be avoided. Once the distal end of the K-wire/guidewire is positioned in a desired location/region, the elongated probe may be withdrawn while leaving the K-wire/guidewire in place. Thereafter, additional instrumentation and/or assemblies may be introduced to the anatomical location/region using the K-wire/guidewire as a guide (e.g., an external ventricular drain (EVD) catheter or ventricular drain to relieve intracranial pressure and hydrocephalus).

In another exemplary embodiment, the disclosed instrument, assembly and method generally includes a handle member and an elongated probe that is adapted to mount with respect to (or otherwise cooperate with) the handle member. The elongated probe includes an ultrasound transducer positioned at or near a distal end thereof. The ultrasound transducer is typically directed in either a perpendicular or substantially perpendicular orientation relative to the axis of the elongated probe, such that non-axial ultrasound imaging is facilitated, or in axial (or substantial axial) alignment with the elongated probe, such that axially-directed ultrasound imaging is facilitated. The handle member of the disclosed instruments/systems generally cooperates with conventional cabling for communication to and with the elongated probe and, in particular, the distally-positioned ultrasound transducer.

In use, the elongated probe of the disclosed instrument/assembly is adapted to receive a tubular member (e.g., an EVD catheter or a ventricular drain) therearound for delivery thereof to a desired anatomical region/location. The tubular member extends axially alongside the elongated probe and is configured and dimensioned so as to permit unobstructed ultrasound imaging. Thus, in exemplary embodiments, the tubular member includes an opening, channel, window or other structural feature that permits unobstructed ultrasound imaging from the ultrasound transducer, whether such ultrasound imaging is directed axially, transversely or at some other orientation relative to the elongated probe/member. In alternative implementations, the distal end of the tubular member is positioned proximal of the ultrasound transducer, thereby permitting unobstructed ultrasound imaging from the elongated probe in a desired axial/angular direction. Thus, the tubular member (e.g., EVD catheter/ventricular drain or other tubular/catheter structure) may be introduced to a desired anatomical region/location while ultrasound imaging ensures that injury to adjacent anatomical structures/features is avoided.

Accordingly, the elongated probe with associated tubular member may be advantageously introduced to a desired anatomical region (e.g., into the cranium of a patient) with real-time ultrasound imaging of anatomical structures adjacent thereto. In this way, potential injuries associated with inadvertent contact of the tubular member with adjacent anatomical structures/features may be avoided. Once the distal end of the tubular member reaches a desired location/region, the elongated probe may be withdrawn while leaving the tubular member in place (e.g., to relieve intracranial pressure and hydrocephalus).

In a further exemplary embodiment, the disclosed instrument, assembly and method generally includes a handle member and an elongated probe that is adapted to mount with respect to (or otherwise cooperate with) the handle member. The elongated probe includes an ultrasound transducer positioned at or near a distal end thereof. The ultrasound transducer is typically directed in a perpendicular or substantially perpendicular orientation, or in an axial or substantially axial direction, relative to the axis of the elongated probe. The handle member of the disclosed instruments/assemblies generally cooperates with conventional cabling for communication to and with the elongated probe and, in particular, the distally-positioned ultrasound transducer. In use, the elongated probe of the disclosed instrument/assembly may be introduced to a desired anatomical region/location and the associated ultrasound imaging may be used to evaluate blood flow and/or flow velocities (e.g., during cranial aneurysm procedures/surgery, vascular procedures/surgery, intra-cranial procedures/surgery, extra-cranial procedures/surgery, bypass procedures/surgery, tumor-related procedures/surgery, and the like).

In another exemplary embodiment, the disclosed instrument, assembly and method generally includes a handle member and an elongated probe that is adapted to mount with respect to (or otherwise cooperate with) the handle member. The elongated probe includes an ultrasound transducer positioned at or near a distal end thereof. The ultrasound transducer is typically directed in a perpendicular or substantially perpendicular orientation, or in an axial or substantially axial orientation, relative to the axis of the elongated probe. The elongated probe further includes one or more integrated and/or modular accessory items positioned at or near and extending from a distal end thereof. The integrated/modular items that may be associated with the disclosed elongated probe include, without limitation, such items as a curette, a probe, a knife, a suction device, a scissor, a cautery unit, forceps, a grasping device and the like. Thus, for example, a curette may be provided that generally defines a tissue cutting element which can be used, for example, to resect tissue (e.g., a tumor). The operation and use of other integrated/modular items are known and understood by persons skilled in the art and are not discussed/described further herein. The handle member of the disclosed instruments/assemblies generally cooperates with conventional cabling for communication to and with the elongated probe and, in particular, the distally-positioned ultrasound transducer.

In use, the elongated probe may be advantageously introduced to a desired anatomical region with real-time ultrasound imaging (e.g., to localize the pituitary gland and surrounding structures). The elongated probe may include one or more integrated/modular items for use in the diagnostic/surgical procedure. Thus, for example, a curette with a tissue cutting element may be used to resect tissue (e.g., to remove pituitary tumors while observing the extent of resection through ultrasound imaging). The disclosed device/assembly may also be used to explore for residual tumor and visualize cavernous sinus contents (e.g., using color and power Doppler functionalities).

According to the present disclosure, it is further contemplated that the disclosed instruments/assemblies may be used in conjunction with an endoscope and/or endoscopic camera, thereby permitting simultaneous ultrasound imaging and conventional viewing. Thus, the elongated probe/member may be adapted to cooperate with an endoscopic element that transmits images for viewing by medical personnel, thereby augmenting the ultrasound imaging delivered by the ultrasound transducer associated with the elongated probe/member. In addition, the disclosed elongated probe/member may include one or more fiducials (e.g., flats or notches) or other antennae that may allow for the handle member and/or elongated probe/member to be monitored/viewed by conventional neuro-navigation systems. In this way, the disclosed devices/assemblies may be advantageously integrated into intra-operative navigation systems, such as brain lab or stealth systems, so that the disclosed device/assembly may serve as a pointer for intra-operative navigation systems while also giving real-time feedback using ultrasound, which optionally may be merged with pre-operative MRI or CT scans.

The present disclosure provides for an ultrasound assembly including an elongated probe extending from a proximal end to a distal end, the proximal end extending from and mounted with respect to a handle member, the elongated probe supporting an ultrasound transducer configured to obtain ultrasound images to determine a location of the elongated probe relative to surrounding anatomical structures or features, the ultrasound transducer including an array of ultrasonic energy generation elements; and a detachable surgical device positioned proximal to and detachably mounted to an outer periphery of the distal end of the elongated probe, the detachable surgical device including a housing section and a protruding section with the housing section having a first window member configured to align with and expose the ultrasound transducer; wherein the elongated probe, ultrasound transducer and detachable surgical device are cooperatively configured, oriented and dimensioned to allow an operator to insert the detachable surgical device and the distal end of the elongated probe into a desired anatomical location to permit the operator to: (i) perform thereat a surgical procedure of the desired anatomical location by utilizing the detachable surgical device mounted to the outer periphery of the distal end of the elongated probe, and (ii) obtain ultrasound imaging of the desired anatomical location via the exposed ultrasound transducer.

The present disclosure also provides for an ultrasound assembly wherein the protruding section extends from the housing section and includes a curette member having a tissue cutting element. The present disclosure also provides for an ultrasound assembly wherein the protruding section extends from the housing section; and wherein the protruding section includes an instrument selected from a group consisting of a curette, a probe, a knife, a suction device, a scissor, a cautery unit, forceps and a grasping device.

The present disclosure also provides for an ultrasound assembly wherein the housing section of the detachable surgical device is hollow and substantially cylindrical, and defines a lumen within the housing section. The present disclosure also provides for an ultrasound assembly wherein the lumen is configured and dimensioned to house the outer periphery of the distal end of the elongated probe.

The present disclosure also provides for an ultrasound assembly wherein the housing section further includes a second window member configured to align with and expose the ultrasound transducer. The present disclosure also provides for an ultrasound assembly wherein the first and second window members are spaced equidistantly apart from one another on the housing section. The present disclosure also provides for an ultrasound assembly wherein after the detachable surgical device is detachably mounted to the distal end of the elongated probe so that first window member is positioned above the ultrasound transducer for substantially unobstructed ultrasound imaging through the first window member, a user can then circumferentially rotate the detachable surgical device around the probe until the second window member is positioned above the ultrasound transducer for substantially unobstructed ultrasound imaging through the second window member.

The present disclosure also provides for an ultrasound assembly wherein a distal end of the housing section includes a distal annular section, and a proximal end of the housing section includes a proximal annular section; and wherein the distal and proximal annular sections are configured and dimensioned to surround and house the outer periphery of the distal end of the elongated probe.

The present disclosure also provides for an ultrasound assembly wherein a distal end of the housing section includes an abutment surface that is configured and dimensioned to abut against the distal end of the elongated probe. The present disclosure also provides for an ultrasound assembly wherein the protruding section of the detachable surgical device extends from a distal end of the housing section.

The present disclosure also provides for an ultrasound assembly wherein the handle member defines a guide channel that is sized and configured for receipt of a K-wire or guidewire; and wherein the guide channel is sized and configured to permit the K-wire or guidewire to run alongside the elongated probe. The present disclosure also provides for an ultrasound assembly further including at least one hollow receiver member mounted with respect to the elongated probe; wherein the at least one hollow receiver member is configured and dimensioned to receive a K-wire or guidewire. The present disclosure also provides for an ultrasound assembly wherein the at least one hollow receiver member includes a first hollow receiver member and a second hollow receiver member mounted with respect to the elongated probe, each hollow receiver member configured and dimensioned to receive the K-wire or guidewire; and wherein the first hollow receiver member is mounted with respect to a distal portion of the elongated probe and the second hollow receiver member is mounted with respect to a proximal end of the elongated probe. The present disclosure also provides for an ultrasound assembly wherein the at least one hollow receiver member extends from a distal portion of the elongated probe to a proximal end of the elongated probe.

The present disclosure also provides for an ultrasound assembly including an elongated probe extending from a proximal end to a distal end, the proximal end extending from and mounted with respect to a handle member, the elongated probe supporting an ultrasound transducer configured to obtain ultrasound images to determine a location of the elongated probe relative to surrounding anatomical structures or features, the ultrasound transducer including an array of ultrasonic energy generation elements; and a detachable surgical device positioned proximal to and detachably mounted to an outer periphery of the distal end of the elongated probe, the detachable surgical device including a housing section and a protruding section with the housing section having: (i) a first window member configured to align with and expose the ultrasound transducer when the detachable surgical device is in a first mounted position relative to the elongated probe, and (ii) a second window member configured to align with and expose the ultrasound transducer when the detachable surgical device is in a second mounted position relative to the elongated probe; wherein the elongated probe, ultrasound transducer and detachable surgical device are cooperatively configured, oriented and dimensioned to allow an operator to insert the detachable surgical device and the distal end of the elongated probe into a desired anatomical location to permit the operator to: (i) perform thereat a surgical procedure of the desired anatomical location by utilizing the detachable surgical device mounted to the outer periphery of the distal end of the elongated probe, and (ii) obtain ultrasound imaging of the desired anatomical location via the exposed ultrasound transducer when the detachable surgical device is in the first or second mounted position relative to the elongated probe.

The present disclosure also provides for an ultrasound assembly wherein the protruding section extends from a distal end of the housing section and includes a curette member having a tissue cutting element. The present disclosure also provides for an ultrasound assembly wherein the housing section of the detachable surgical device is hollow and substantially cylindrical, and defines a lumen within the housing section; and wherein the lumen is configured and dimensioned to house the outer periphery of the distal end of the elongated probe.

The present disclosure also provides for an ultrasound assembly wherein the distal end of the housing section includes a distal annular section, and a proximal end of the housing section includes a proximal annular section; wherein the distal and proximal annular sections are configured and dimensioned to surround and house the outer periphery of the distal end of the elongated probe; and wherein the distal end of the housing section includes an abutment surface that is configured and dimensioned to abut against the distal end of the elongated probe.

The present disclosure also provides for a method for performing a procedure, including providing an elongated probe extending from a proximal end to a distal end, the elongated probe supporting an ultrasound transducer; detachably mounting a surgical device to an outer periphery of the distal end of the elongated probe, the detachably mounted surgical device including a housing section and a protruding section with the housing section having a window member configured to align with and expose the ultrasound transducer; introducing and inserting the elongated probe, the exposed ultrasound transducer, and the detachably mounted surgical device to a desired anatomical location while obtaining ultrasound images, via the exposed ultrasound transducer, for use in assessing the position of the elongated probe and the detachably mounted surgical device relative to surrounding anatomical structures; performing a surgical procedure of the desired anatomical location by utilizing the detachably mounted surgical device; and obtaining ultrasound imaging, via the exposed ultrasound transducer, of the desired anatomical location for the surgical procedure.

Any combination or permutation of embodiments is envisioned. Additional advantageous features, functions and applications of the disclosed assemblies, systems and methods of the present disclosure will be apparent from the description which follows, particularly when read in conjunction with the appended figures. For example, the disclosed devices, assemblies and methods may be used in conjunction with conventional technologies (e.g., microscopic and/or endoscopic visualization) to further enhance clinical efficacy. All references listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure. To assist those of ordinary skill in the art in making and using the disclosed systems, assemblies and methods, reference is made to the appended figures, wherein:

FIG. 18 is a side perspective view of an exemplary detachable device configured to mount with respect to various elongated probes and/or ultrasound assemblies;

FIG. 19 is a top view of the device of FIG. 18;

FIG. 20 is a cross-sectional view of the device of FIG. 19 taken along the line C-C;

FIG. 21 is a left-side view of the device of FIG. 18;

FIG. 22 is a right-side view of the device of FIG. 18;

FIG. 23 is a partial top left-side perspective view of the device of FIG. 18;

FIG. 24 is a side perspective view of another exemplary detachable device configured to mount with respect to various elongated probes and/or ultrasound assemblies;

FIG. 25 is a top view of the device of FIG. 24;

FIG. 26 is a cross-sectional view of the device of FIG. 25 taken along the line C-C;

FIG. 27 is a left-side view of the device of FIG. 24;

FIG. 28 is a right-side view of the device of FIG. 24;

DETAILED DESCRIPTION OF DISCLOSURE

Figure 1:
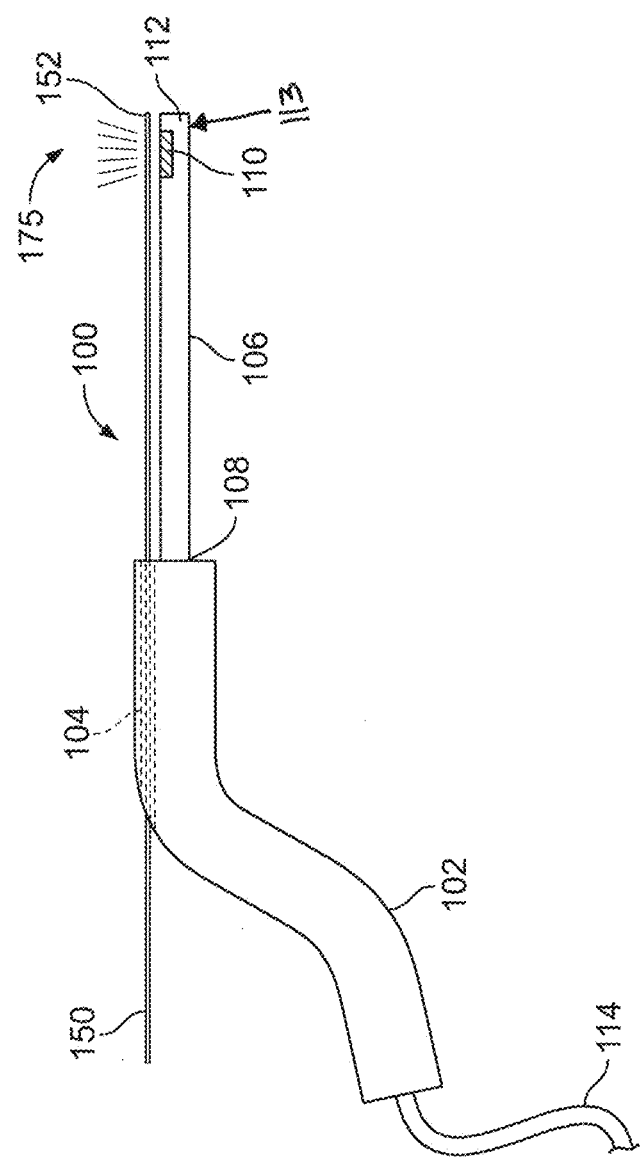
FIG. 1 is a side view of an exemplary ultrasound assembly in cooperation with a K-wire/guidewire according to the present disclosure.
Figure 2:
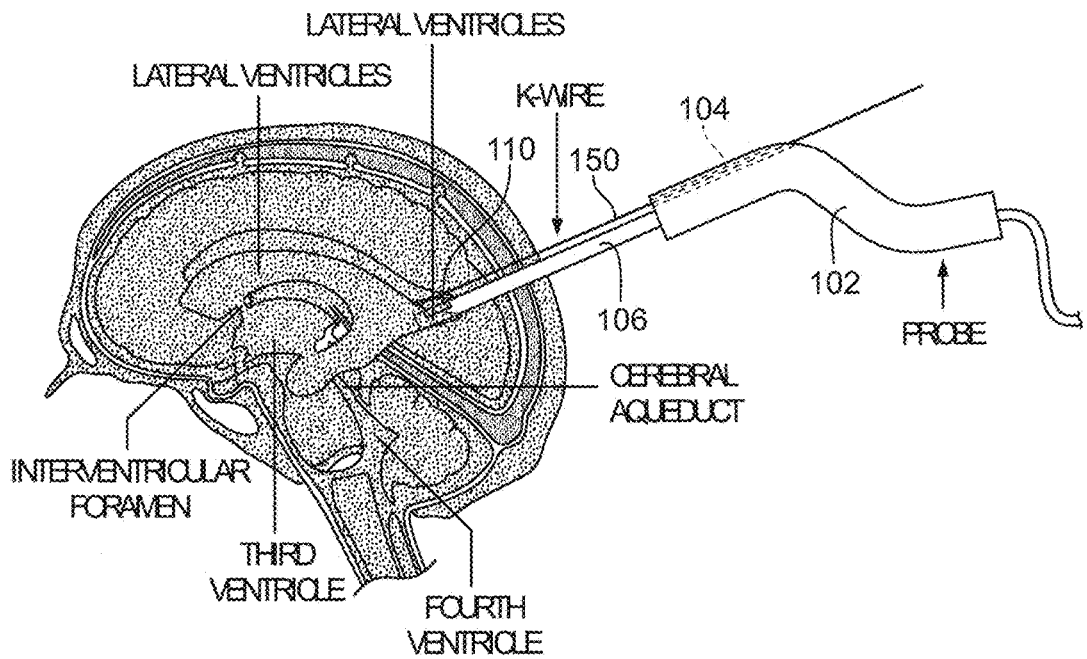
FIG. 2 is a schematic depiction of the exemplary assembly of FIG. 1 showing guidance to a desired anatomical location/region.
Figure 3:
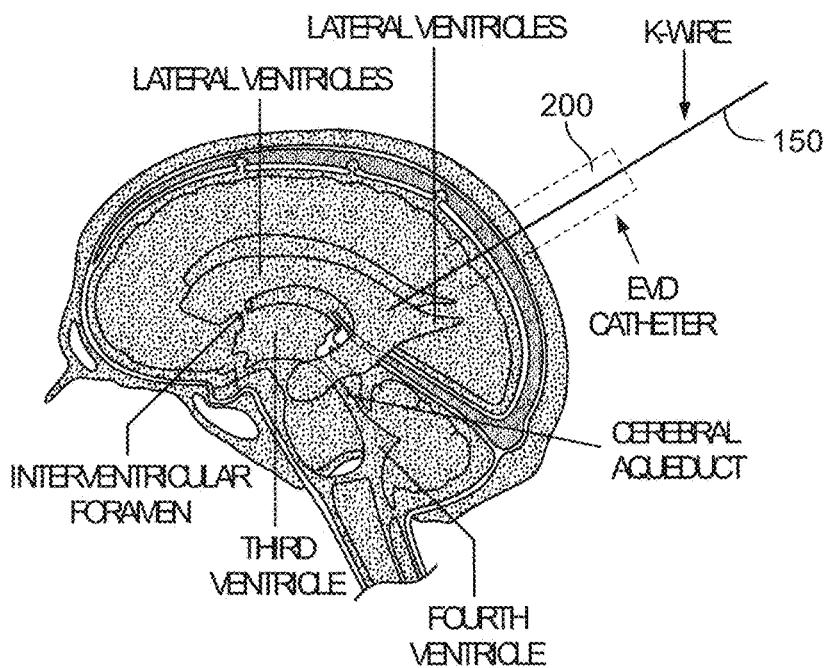
FIG. 3 is a further schematic depiction in which the exemplary ultrasound assembly of the present disclosure has been withdrawn from the anatomical location/region, and the K-wire/guidewire is used to guide an EVD catheter/ventricular drain to such anatomical location/region.
Figure 4:
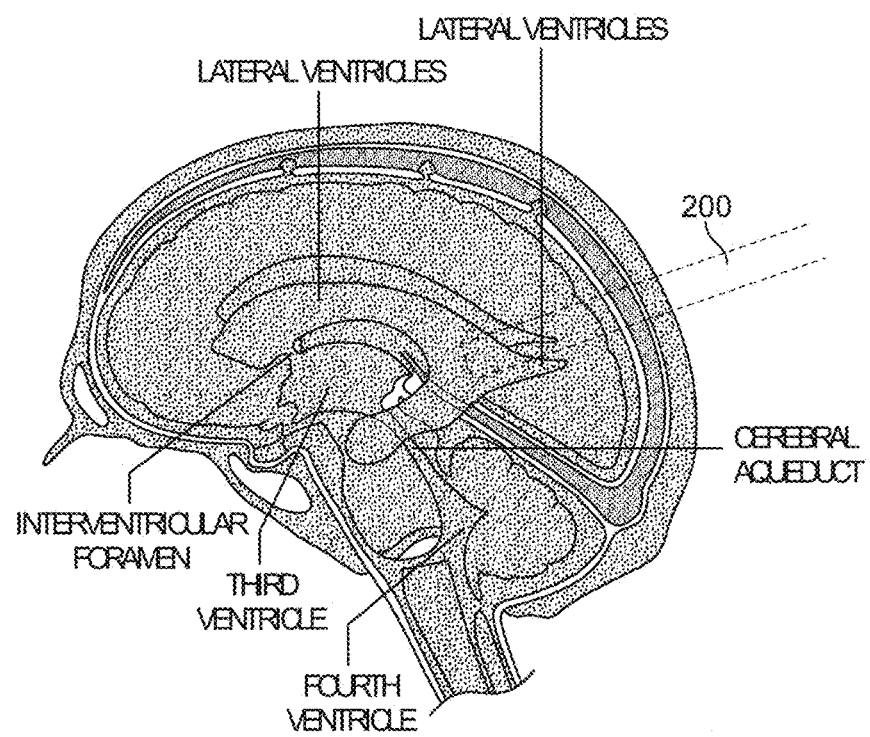
FIG. 4 is a further schematic depiction in which, as compared to the schematic depiction of FIG. 3, the K-wire/guidewire has now been withdrawn leaving the EVD catheter/ventricular drain in position.

The exemplary embodiments disclosed herein are illustrative of advantageous ultrasound assemblies, and systems of the present disclosure and methods/techniques thereof. It should be understood, however, that the disclosed embodiments are merely exemplary of the present disclosure, which may be embodied in various forms. Therefore, details disclosed herein with reference to exemplary ultrasound assemblies/fabrication methods and associated processes/techniques of assembly and use are not to be interpreted as limiting, but merely as the basis for teaching one skilled in the art how to make and use the advantageous ultrasound assemblies/systems and/or alternative ultrasound assemblies of the present disclosure.

In accordance with embodiments of the present disclosure, advantageous medical diagnostic and surgical instruments, assemblies and methods are provided for use during a broad variety of clinical applications and procedures (e.g., procedures within the cranium and/or in connection with and/or in proximity to the brain, spinal surgical procedures, orthopedic applications, minimally invasive surgical procedures, etc.).

Referring now to the drawings, like parts are marked throughout the specification and drawings with the same reference numerals, respectively. Drawing figures are not necessarily to scale and in certain views, parts may have been exaggerated for purposes of clarity.

Referring now to FIGS. 1-4, an exemplary ultrasound assembly 100 generally includes a handle member 102 that defines guide wire channel 104 and an elongated probe 106 that is adapted to mount with respect to (or otherwise cooperate with) the handle member 102. In exemplary embodiments of the present disclosure, the elongated probe 106 may be detachably mounted with respect to handle member 102, e.g., by way of a bayonet locking mechanism, in junction region 108. Appropriate electrical connections are generally made in the junction region 108 to facilitate electronic communications between the handle member 102 (and accessory componentry/power source) and the elongated probe 106 (and associated operative functionalities).

The elongated probe 106 includes an ultrasound transducer 110 positioned at or near a distal end 112 thereof. In the embodiment depicted in FIGS. 1-4, the ultrasound transducer 110 is directed in a perpendicular or substantially perpendicular orientation relative to the axis of the elongated probe 106, such that non-axial ultrasound imaging is facilitated. However, the disclosed device may alternatively be provided with a ultrasound transducer that is positioned so as to be axially or substantially axially oriented with respect to the axis defined by elongated probe 106. The handle member 102 of the ultrasound assembly 100 generally cooperates with conventional cabling 114 for communication to and with the elongated probe 106 and, in particular, the distally-positioned ultrasound transducer 110. In exemplary embodiments, the ultrasound transducer 110 includes an array of ultrasonic energy generation elements.

In use, the handle member 102 of ultrasound assembly 100 is adapted to receive a K-wire/guidewire 150 (or other elongated structure) through the guide channel 104 defined therein. The K-wire/guidewire may take various forms and exhibit various properties (e.g., it may be sharp/blunt, rigid/flexible, threaded (in whole or in part), etc.). The K-wire/guidewire 150 extends axially alongside the elongated probe 106 such that its distal end 152 may be positioned in close proximity to the region 175 under ultrasound imaging. Thus, in exemplary embodiments, the handle 102 is configured and dimensioned such that a stepped geometry is defined in the junction region 108. The guide channel 104 is formed in the outwardly stepped region of the handle 102, such that a K-wire/guidewire 150 that passes through the guide channel 104 can easily run alongside the elongated probe 106 in a substantially linear fashion.

The elongated probe 106 with associated K-wire/guidewire 150 may be advantageously introduced to a desired anatomical region (e.g., into the cranium of a patient) with real-time ultrasound imaging of anatomical structures adjacent thereto. In this way, potential injuries associated with inadvertent contact of the K-wire/guidewire 150 with adjacent anatomical structures/features may be avoided. Once the distal end 152 of the K-wire/guidewire 150 is positioned in a desired location/region, the elongated probe 106 may be withdrawn while leaving the K-wire/guidewire 150 in place. Thereafter, additional instrumentation and/or assemblies may be introduced to the anatomical location/region using the K-wire/guidewire 150 as a guide (e.g., a tubular member 200 such as an external ventricular drain (EVD) catheter/ventricular drain 200 to relieve intracranial pressure and/or hydrocephalus).

Figure 15:
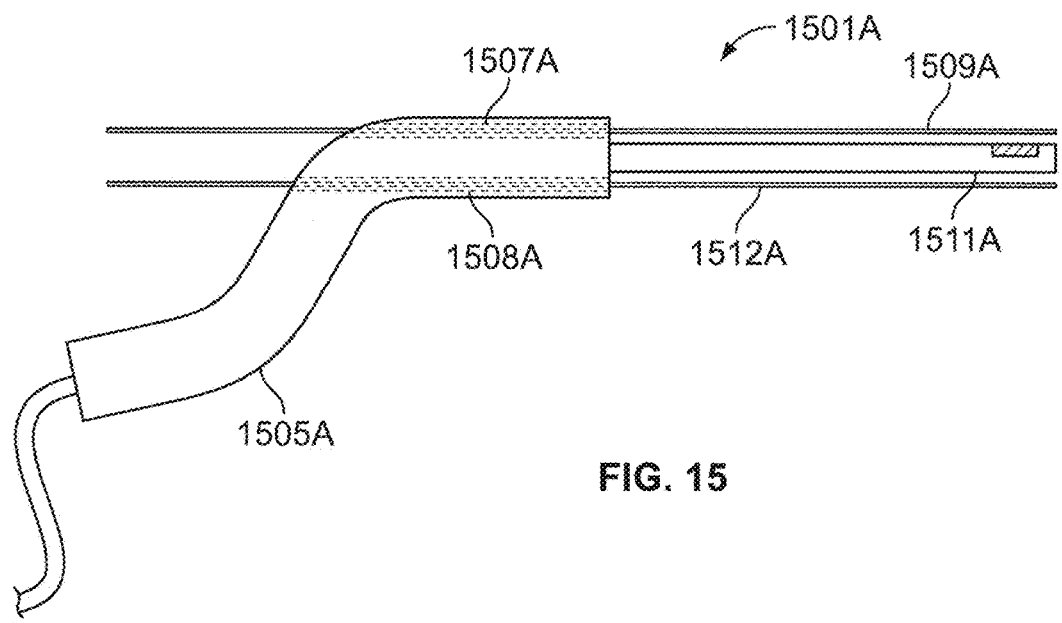
FIG. 15 is a side elevational view of an exemplary embodiment of an ultrasound assembly similar to the assembly of FIG. 1 in accordance with the present disclosure for use in conjunction with K-wires/guidewires (that may be introduced through alternative channels)

With reference to FIG. 15, an alternative ultrasound assembly 1501A is shown. The assembly 1501A may be structurally and functionally similar to the ultrasound assembly 100 discussed above with reference to FIG. 1, with certain additional features. In general, handle member 1505A of ultrasound assembly 1501A defines first channel 1507A and second channel 1508A. In general, the channels 1507A and 1508A are formed in the handle member 1505A and extend therethrough. Both channels 1507A and 1508A are configured and dimensioned to receive a K-wire/guidewire, e.g., K-wire 1509A and/or K-wire 1512A, to permit the ultrasound assembly 1501A to be slidably mounted thereto for purposes of guiding the assembly 1501A to a desired anatomical region (e.g., into the cranium of a patient) with real-time ultrasound imaging of anatomical structures adjacent thereto. Once the distal ends of the K-wires/guidewires 1509A and/or 1512A are positioned in a desired location/region, the elongated probe 1511A may be withdrawn while leaving K-wires/guidewires 1509A and/or 1512A in place, as described above. In one embodiment, the operator/surgeon would be free to select the channel 1507A and/or 1508A to be used for K-wire introduction.

Figure 16:
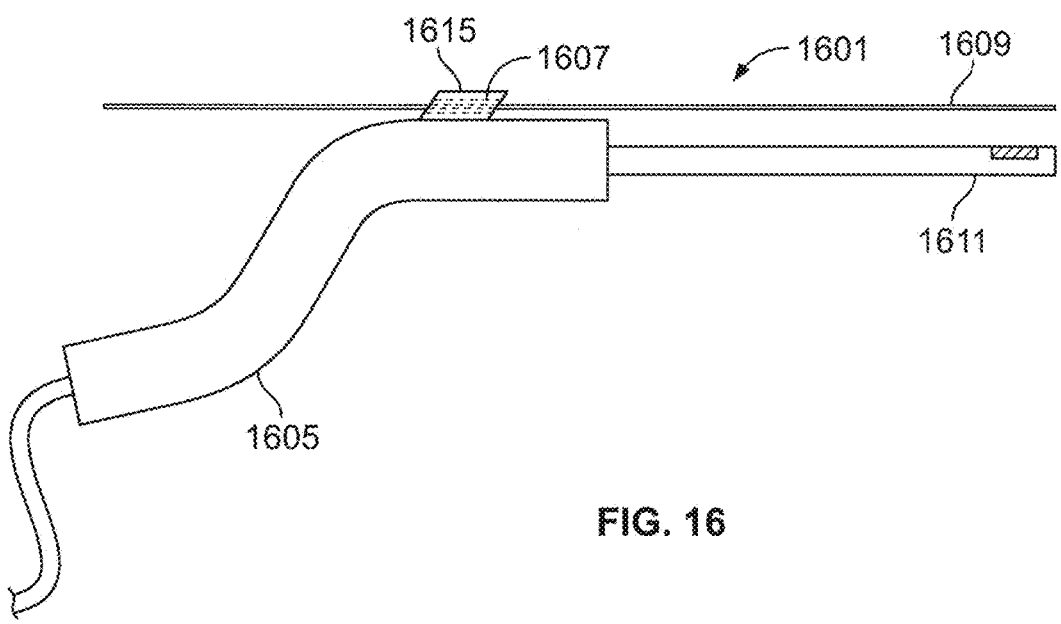
FIG. 16 is a side elevational view of another exemplary embodiment of an ultrasound assembly in accordance with the present disclosure for use in conjunction with a K-wire/guidewire.

Turning now to FIG. 16, an ultrasound assembly 1601 in accordance with embodiments of the present disclosure is shown. The ultrasound assembly 1601 may be structurally and functionally similar to the ultrasound assembly 100 discussed above with reference to FIG. 1, with certain additional features. A channel 1607 is configured and dimensioned to receive a K-wire/guidewire 1609 to permit the ultrasound assembly 1601 to be slidably mounted thereto for purposes of guiding the assembly 1601 and/or elongated probe 1611 to a desired anatomical region (e.g., into the cranium of a patient), the channel 1607 being formed in an extension 1615 of the handle member 1605 and extending past the handle member 1605.

Figure 17:
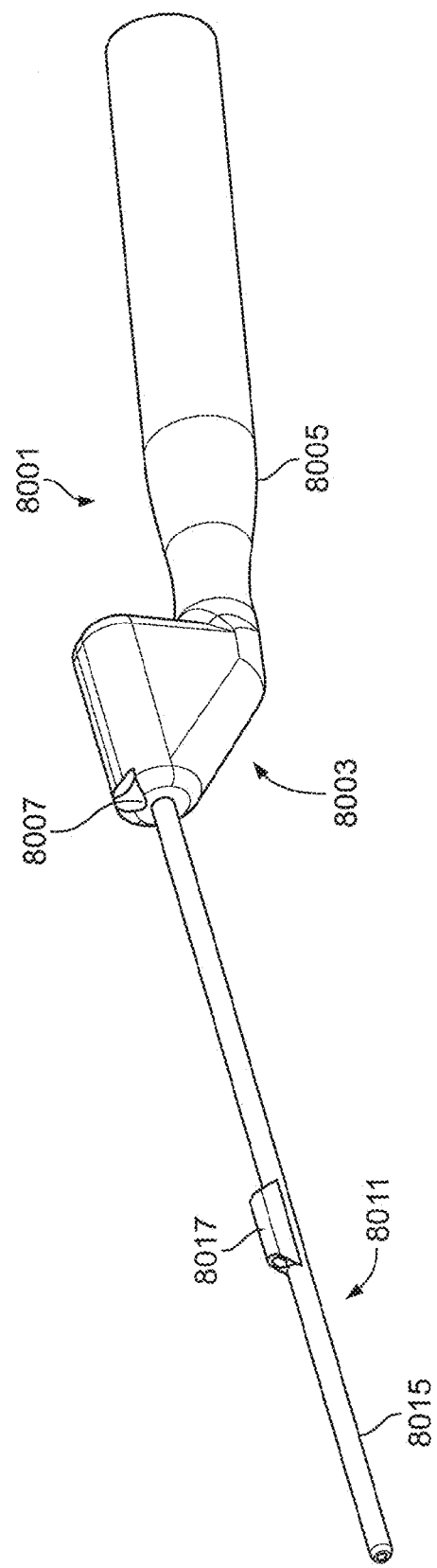
FIG. 17 is a side perspective view of another exemplary embodiment of an assembly in accordance with the present disclosure for use in conjunction with a K-wire/guidewire.

With reference to FIG. 17, an ultrasound assembly 8001 in accordance with embodiments of the present disclosure is shown. Ultrasound assembly 8001 may be structurally and functionally similar to the ultrasound assembly 100 discussed above with reference to FIG. 1, with some differences. In general, ultrasound assembly 8001 includes at least one hollow receiver member 8017 mounted with respect to longitudinal shaft 8015 of elongated probe 8011. In general, the at least one hollow receiver member 8017 is configured and dimensioned to receive a K-wire or guidewire or the like (e.g., a wire similar to K-wire 150 of FIG. 1) to permit the assembly 8001 to be slidably mounted thereto for purposes of guiding assembly 8001 to a desired anatomical region (e.g., into the cranium of a patient) with real-time ultrasound imaging of anatomical structures adjacent thereto. Once the distal end of the K-wire/guidewire (e.g., a wire similar to K-wire 150 of FIG. 1) is positioned in a desired location/region, the elongated probe 8011 may be withdrawn while leaving K-wire/guidewire in place, as described above.

The elongated probe 8011 typically includes an ultrasound transducer mounted to the longitudinal shaft 8015 proximate the distal end thereof, with the ultrasound transducer typically having an array of side-firing ultrasonic energy generation elements extending along the longitudinal shaft 8015 (similar to assembly 100 of FIG. 1 having ultrasound transducer 110). In one embodiment, the at least one hollow receiver member 8017 is positioned or mounted with respect to a distal portion of the longitudinal shaft 8015 of elongated probe 8011, although the present disclosure is not limited thereto. Rather, the at least one hollow receiver member 8017 may be positioned or mounted to any portion of the longitudinal shaft 8015 of elongated probe 8011.

In one embodiment and as shown in FIG. 17, handle 8003 includes a housing 8005, the housing 8005 including a channel 8007 formed therein, with the channel 8007 also configured and dimensioned to receive the K-wire or guidewire or the like that is received in hollow receiver member 8017 to permit the assembly 8001 to be slidably mounted thereto for purposes of guiding assembly 8001 to a desired anatomical region. In exemplary embodiments, channel 8007 extends through handle 8003.

Alternatively, channel 8007 may be formed in an extension of the housing 8005 of the handle 8003 (e.g., similar to extension 1615 of FIG. 16). In one embodiment, the longitudinal axis defined by channel 8007 is substantially the same as and/or is substantially aligned with the longitudinal axis defined by the at least one hollow receiver member 8017 (e.g., the same K-wire 150 would extend through channel 8007 and receiver member 8017). Alternatively, housing 8005 does not include channel 8007, and the K-wire or the like only travels through the at least one receiver member 8017 to permit the ultrasound assembly 8001 to be slidably mounted thereto for guiding purposes.

Figure 17A:
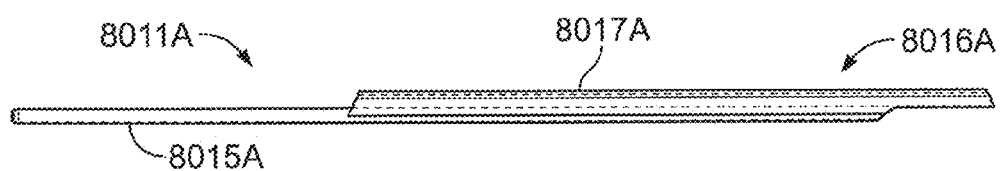
FIGS. 17A and 17B are side elevational views of alternative elongated probes having at least one hollow receiver member mounted thereto for use with an assembly similar to the assembly of FIG. 17.

In another embodiment and as depicted in FIG. 17A, an elongated probe 8011A for use with an ultrasound assembly similar to instrument/assembly 8001 is depicted. At least one hollow receiver member 8017A is mounted with respect to longitudinal shaft 8015A of elongated probe 8011A and extends from a portion (e.g., a distal portion) of the shaft 8015A to a proximal end 8016A of shaft 8015A. In general, hollow receiver member 8017A is configured and dimensioned to receive a K-wire or guidewire or the like to permit the assembly (e.g., ultrasound assembly 8001) to be slidably mounted thereto for guiding purposes.

In exemplary embodiments, the housing (e.g., housing similar to 8005) of the handle of the device for use with elongated probe 8011A may be configured and dimensioned to house and/or mount with respect to at least a portion of the proximal end 8016A of shaft 8015A. For example, at least a portion of the proximal end 8016A of shaft 8015A defines at least a portion of a channel through the housing of the handle of the assembly for use with probe 8011A. The housing of the handle of the assembly for use with elongated probe 8011A may or may not include a separate channel through the handle for use with the K-wire (e.g., separate from proximal end 8016A housed in the housing).

Figure 17B:
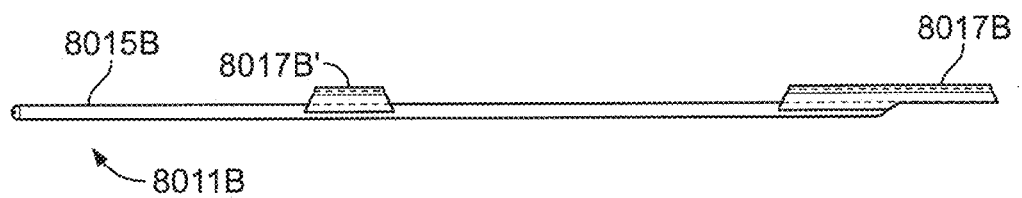
Figure 29:
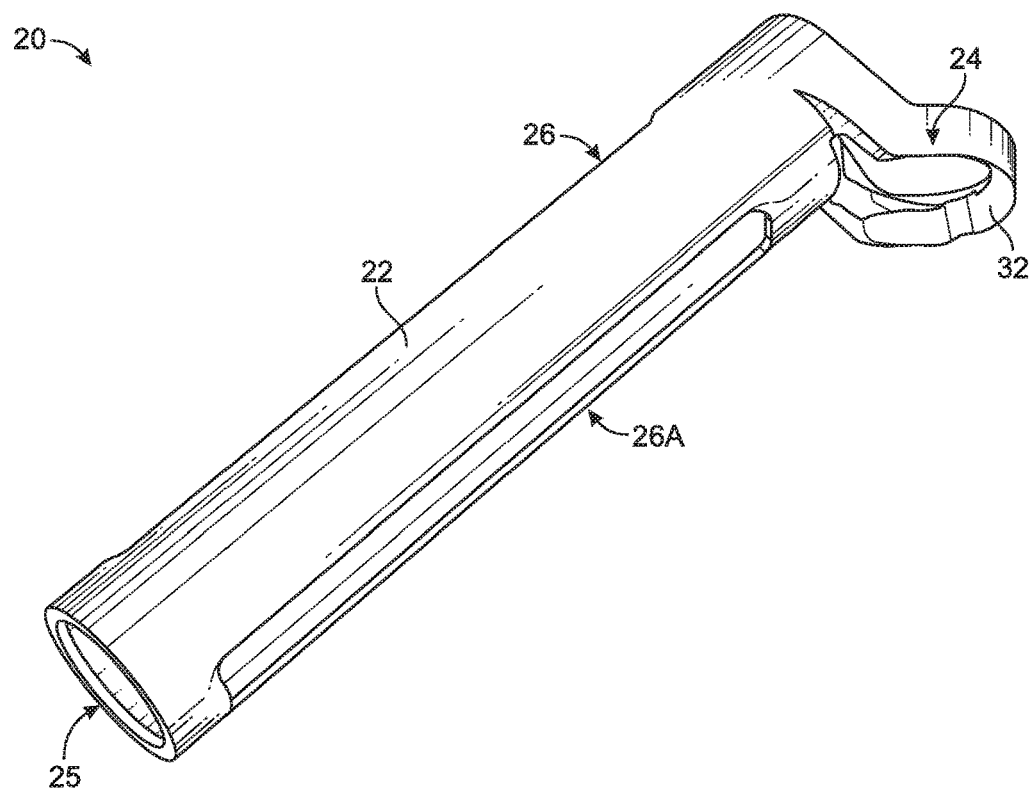
FIG. 29 is another side perspective view of the device of FIG. 18.

In another embodiment and as shown in FIG. 17B, an elongated probe 8011B for use with an assembly similar to ultrasound assembly 8001 is depicted. Elongated probe 8011B includes a first hollow receiver member 8017B and a second hollow receiver member 8017B', with the first and second hollow receiver members 8017B, 8017B' being mounted with respect to longitudinal shaft 8015B of elongated probe 8011B. In general, first and second hollow receiver members 8017B, 8017B' are configured and dimensioned to receive a K-wire or guidewire or the like (e.g., wire 150 of FIG. 1) to permit the assembly to be slidably mounted thereto for guiding purposes.

In one embodiment, first hollow receiver member 8017B is positioned or mounted with respect to a proximal end of probe 8011B, and second hollow receiver member 8017B' is positioned or mounted with respect to a distal portion of probe 8011B, although the present disclosure is not limited thereto. The housing of the handle of the assembly for use with probe 8011B may be configured and dimensioned to house and/or mount with respect to at least a portion of first hollow receiver member 8017B. For example, at least a portion of first hollow receiver member 8017B defines at least a portion of a channel through the housing of the handle of the assembly for use with probe 8011B. The housing of the handle of the assembly for use with probe 8011B may or may not include a separate channel through the handle for use with the K-wire (e.g., separate from first hollow receiver member 8017B housed in the housing). In exemplary embodiments, the longitudinal axis defined by the first hollow receiver member 8017B is substantially the same as and/or is substantially aligned with the longitudinal axis defined by the second hollow receiver member 8017B' (e.g., the same K-wire 150 would extend through first hollow receiver member 8017B and second hollow receiver member 8017B').

Variations and modifications of the above-described devices/assemblies are possible in accordance with embodiments of the present disclosure. In accordance with some such variations and modifications, the handle and the longitudinal shaft of the elongated probe (and/or the longitudinal shaft of the elongated probe and the hollow receiver members) are of unitary construction with respect to each other. Each of the above-described devices/assemblies may be equipped with a cable assembly for carrying electrical signals to and from the ultrasound transducer in accordance with an ultrasonic imaging mode of use of the instrument, the cable assembly including a proximal end including an electrical connector for connecting the instrument to a corresponding ultrasound console and current carrying wires extending distally from the electrical connector to the ultrasound transducer at least partially via a corresponding interior conduit formed in and extending longitudinally along the longitudinal shaft of the ultrasound probe, as explained and described in U.S. Pat. No. 8,343,056 and/or U.S. Pat. No. 8,206,306, the entire contents of each being incorporated by reference herein. It is also noted that other variations and modifications are possible. Thus, the present disclosure provides, inter alia, advantageously integrated medical diagnostic instruments/assemblies, systems incorporating such instruments/assemblies, and methods of use of such instruments/assemblies for the benefit of such surgical practitioners and their patients.

Figure 5:
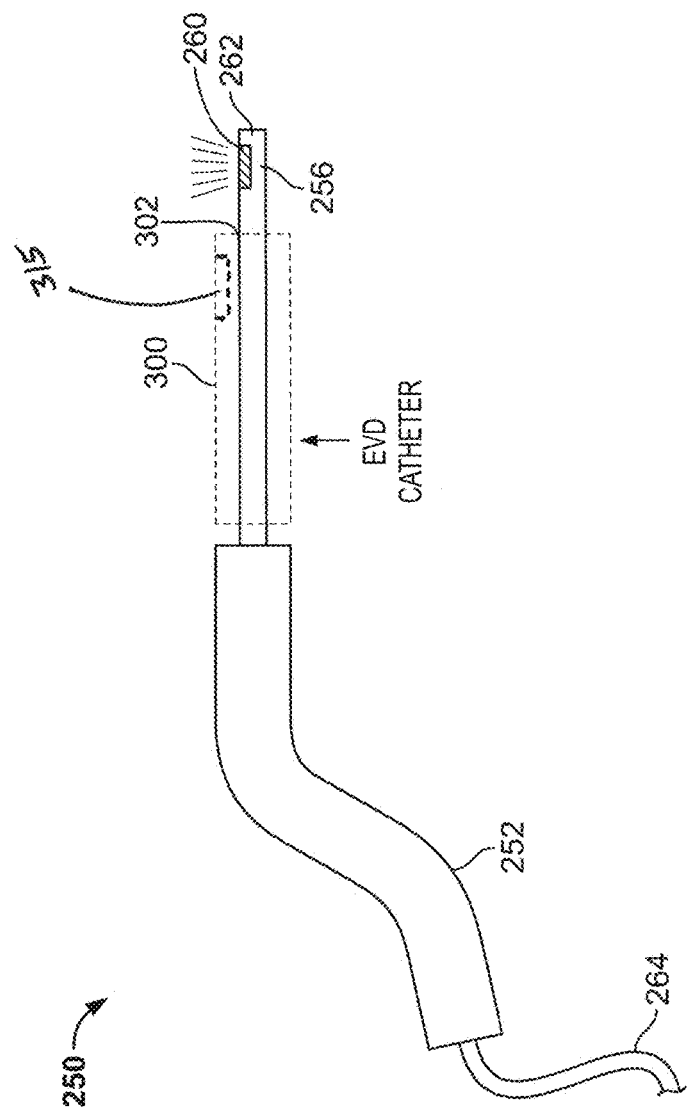
FIG. 5 is a side view of an alternative exemplary ultrasound assembly in cooperation with an EVD catheter/ventricular drain (shown in phantom) according to the present disclosure.
Figure 6:
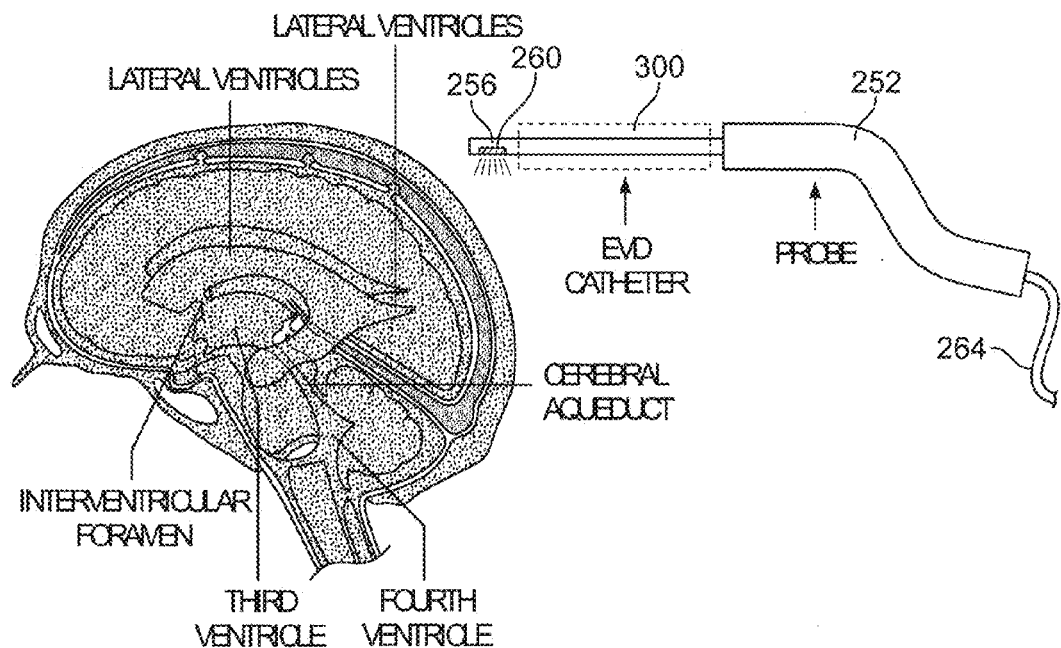
FIG. 6 is a schematic depiction of the exemplary assembly of FIG. 5 showing the assembly with EVD catheter/ventricular drain (shown in phantom) prior to anatomical introduction.
Figure 7:
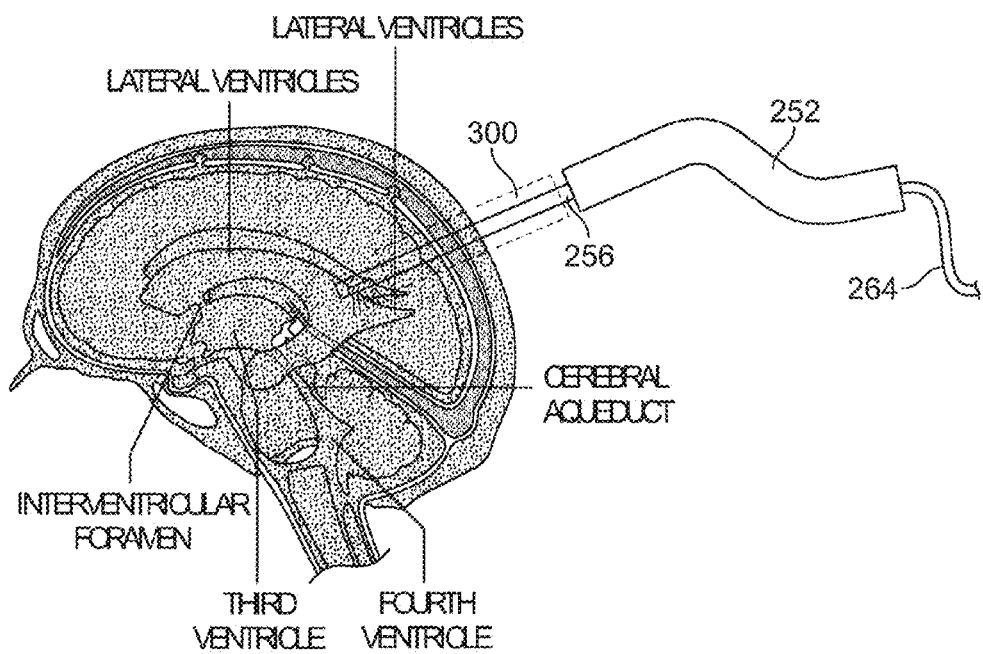
FIG. 7 is a further schematic depiction in which the exemplary assembly of the present disclosure is introduced to a desired the anatomical location/region with the EVD catheter/ventricular drain (shown in phantom) guided to such anatomical location/region thereupon.

In another exemplary embodiment of the present disclosure, ultrasound assembly 250 (FIG. 5) generally includes a handle member 252 and an elongated probe 256 that is adapted to mount with respect to (or otherwise cooperate with) the handle member 252 (e.g., based on a bayonet locking mechanism). The elongated probe 256 includes an ultrasound transducer 260 positioned at or near a distal end 262 thereof. As described above, the ultrasound transducer 260 may be designed in a perpendicular/substantially perpendicular orientation relative to the axis of the elongated probe 256, such that non-axial ultrasound imaging is facilitated, or in an axial/substantially axial orientation relative to the axis of elongated probe 256. The handle member 252 of the assembly 250 generally cooperates with conventional cabling 264 for communication to and with the elongated probe 256 and, in particular, the distally-positioned ultrasound transducer 260.

In use, the elongated probe 256 of ultrasound assembly 250 is adapted to receive a tubular member 300 (e.g., an EVD catheter/ventricular drain 300) therearound for delivery thereof to a desired anatomical region/location. The EVD catheter/ventricular drain 300 extends axially alongside the elongated probe 256 such that its distal end 302 is positioned in close proximity to the ultrasound transducer 260. Thus, as depicted in the accompanying figures, the distal end 302 of the tubular member 300 is positioned proximal of the ultrasound transducer 260, thereby permitting unobstructed ultrasound imaging from the elongated probe 256. In other exemplary embodiments of the present disclosure, however, the distal end 302 of the tubular member 300 is provided with an opening, channel, window or other structural feature 315 that permits unobstructed ultrasound imaging from the ultrasound transducer 260, whether such ultrasound imaging is directed axially, transversely or at some other orientation relative to the elongated member 256. Thus, the tubular member 300 (e.g., EVD catheter 300, or other tubular/catheter structure) may be introduced to a desired anatomical region/location while ultrasound imaging ensures that injury to adjacent anatomical structures/features is avoided.

Figure 8:
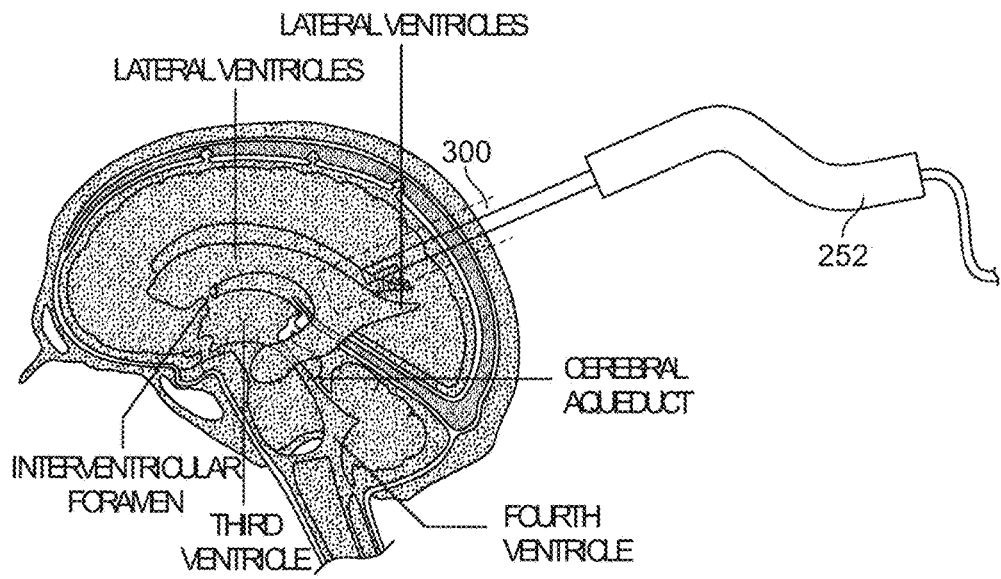
FIG. 8 is a further schematic depiction in which, as compared to the schematic depiction of FIG. 7, the elongated probe is being withdrawn leaving the EVD catheter/ventricular drain in position.
Figure 9:
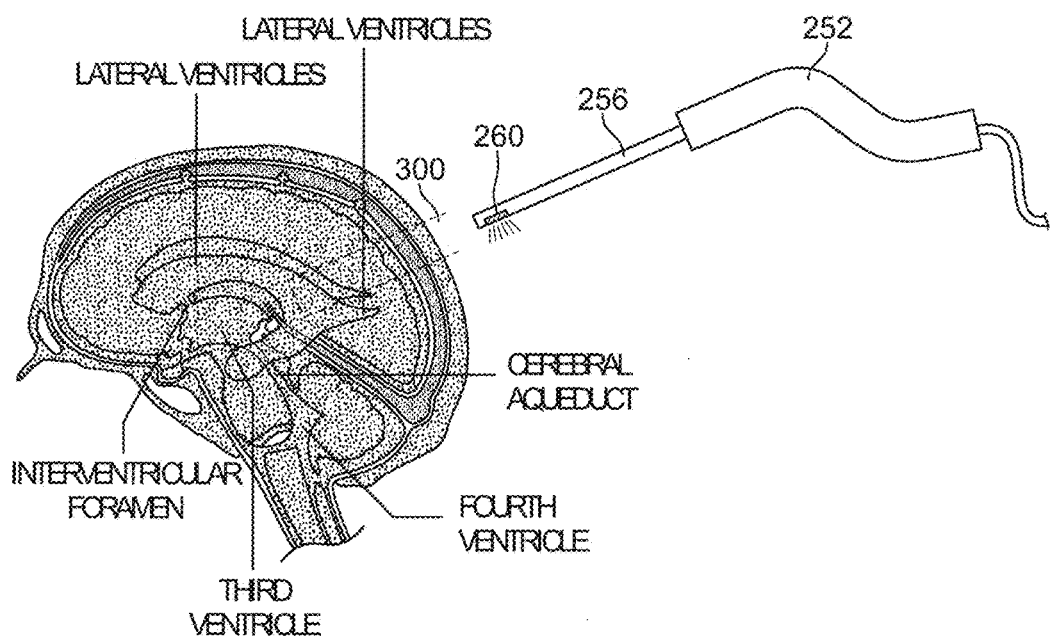
FIG. 9 is a further schematic depiction in which, as compared to the schematic depiction of FIG. 8, the elongated probe is fully withdrawn and the EVD catheter/ventricular drain remains in position.

Accordingly, the elongated probe 256 with associated tubular member 300 may be advantageously introduced to a desired anatomical region (e.g., into the cranium of a patient) with real-time ultrasound imaging of anatomical structures adjacent thereto. In this way, potential injuries associated with inadvertent contact of the tubular member 300 with adjacent anatomical structures/features may be avoided. Once the distal end 302 of the tubular member 300 reaches a desired location/region, the elongated probe 256 may be withdrawn while leaving the tubular member 300 in place (e.g., to relieve intracranial pressure and hydrocephalus (FIGS. 8-9)).

Figure 10:
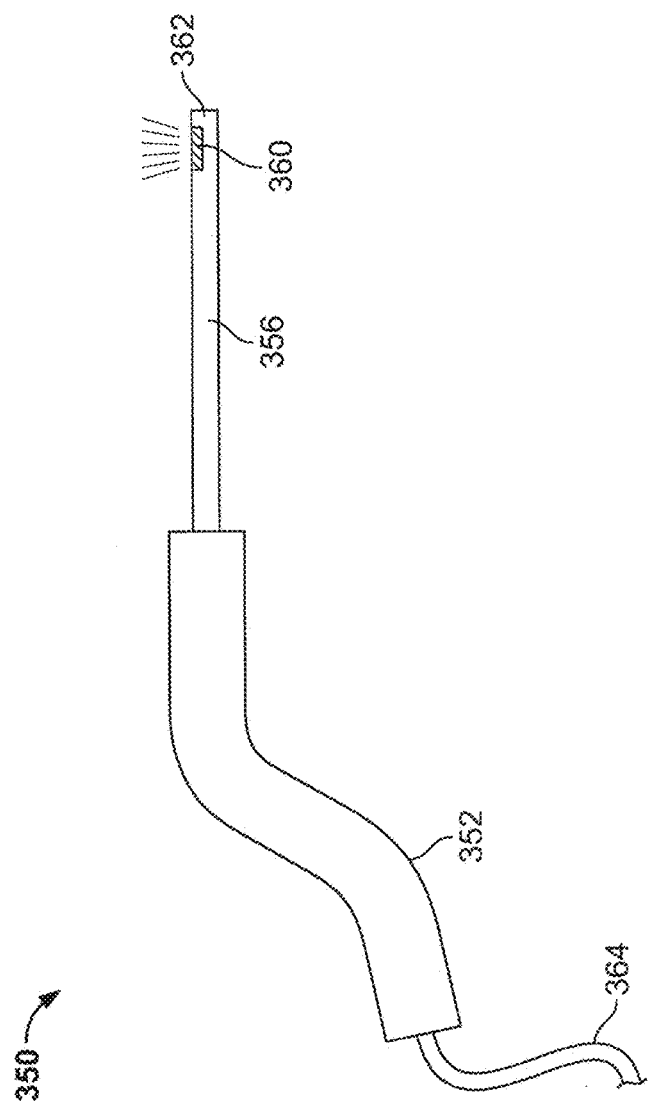
FIG. 10 is a side view of a still further alternative exemplary ultrasound assembly according to the present disclosure.
Figure 11:
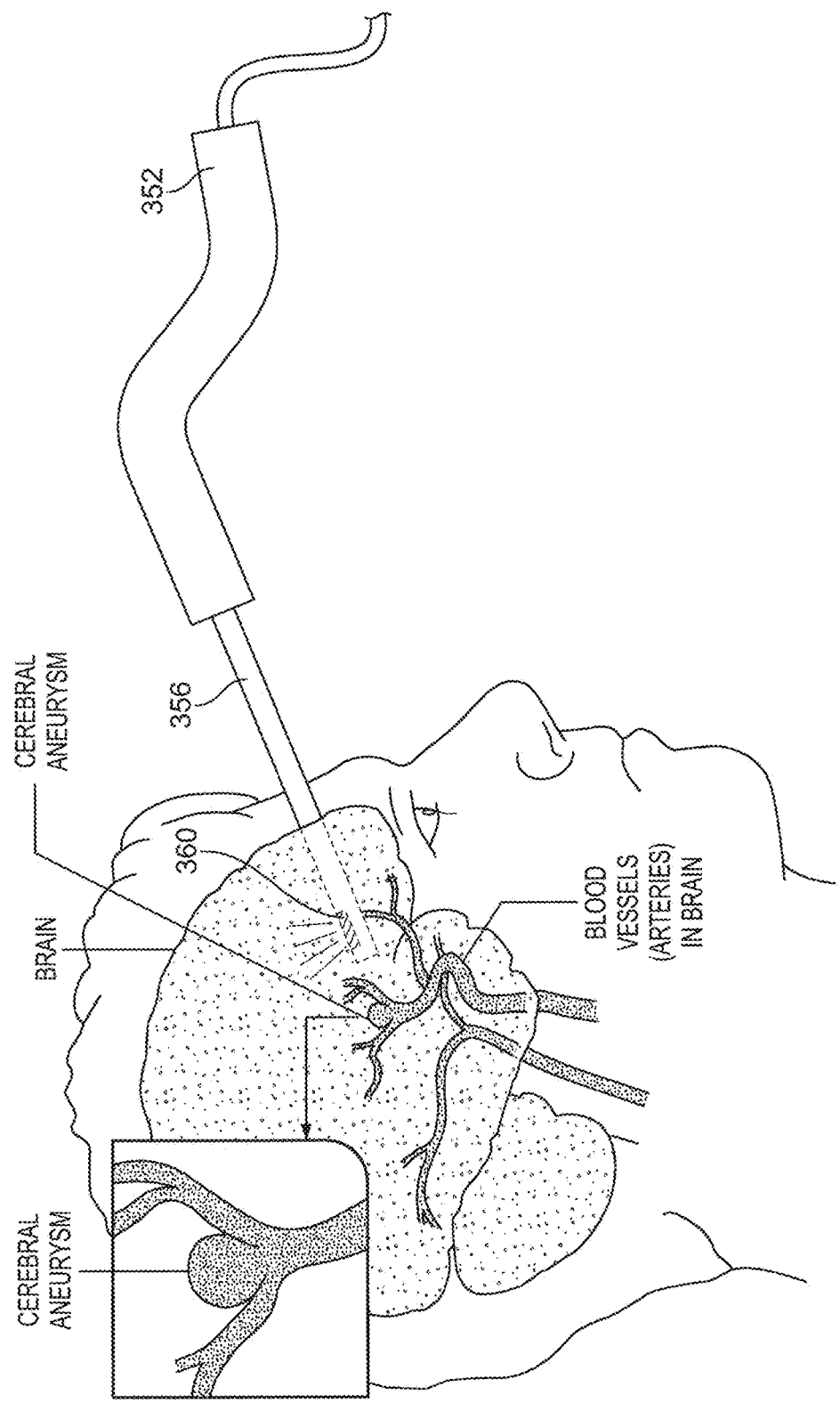
FIG. 11 is a schematic depiction of the exemplary assembly of FIG. 10 showing the assembly positioned at a desired anatomical region/location.

In a further exemplary embodiment of the present disclosure, ultrasound assembly 350 (FIG. 10) generally includes a handle member 352 and an elongated probe 356 that is adapted to mount with respect to (or otherwise cooperate with) the handle member 352. The elongated probe 356 includes an ultrasound transducer 360 positioned at or near a distal end 362 thereof. As with previous embodiments disclosed herein, the ultrasound transducer 360 may be directed in a perpendicular or substantially perpendicular orientation relative to the axis of the elongated probe 356, such that non-axial ultrasound imaging is facilitated, or in an axial or substantially axially orientation relative to the axis of the elongated probe 356. The handle member 352 of assembly 350 generally cooperates with conventional cabling 364 for communication to and with the elongated probe 356 and, in particular, the distally-positioned ultrasound transducer 360. In use, the elongated probe 356 of ultrasound assembly 350 may be introduced to a desired anatomical region/location and the associated ultrasound imaging may be used to evaluate blood flow and/or flow velocities (e.g., during cranial aneurysm procedures/surgery, vascular procedures/surgery, intra-cranial procedures/surgery, extra-cranial procedures/surgery, bypass procedures/surgery, tumor-related procedures/surgery, and the like).

Figure 12:
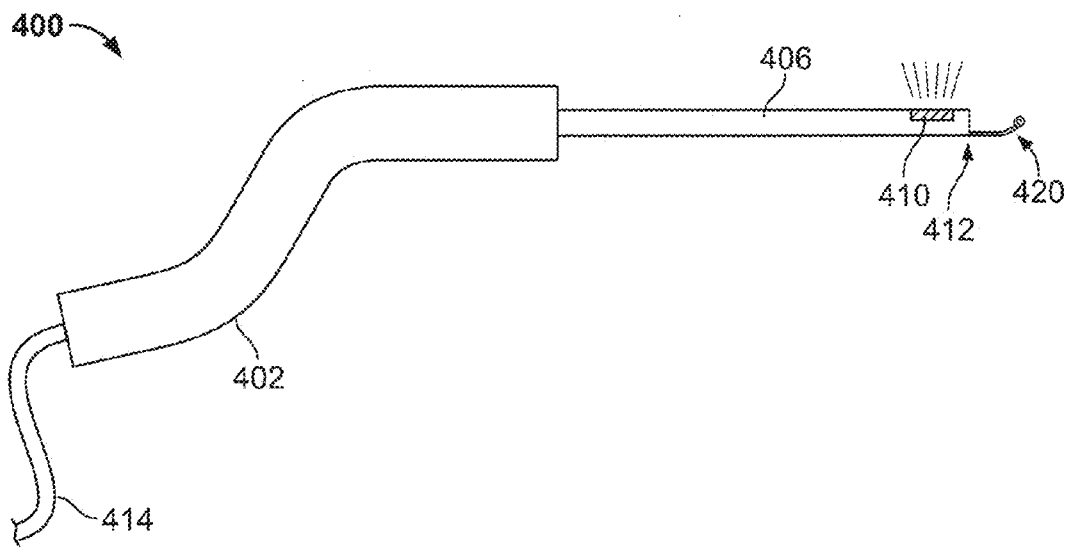
FIG. 12 is a side view of an additional alternative exemplary ultrasound assembly according to the present disclosure.
Figure 13:
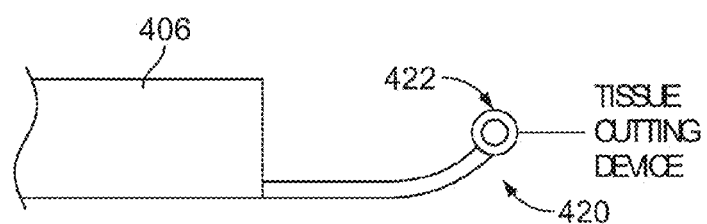
FIG. 13 is a partial view of an exemplary curette that may be associated with the assembly of FIG. 12.
Figure 14:
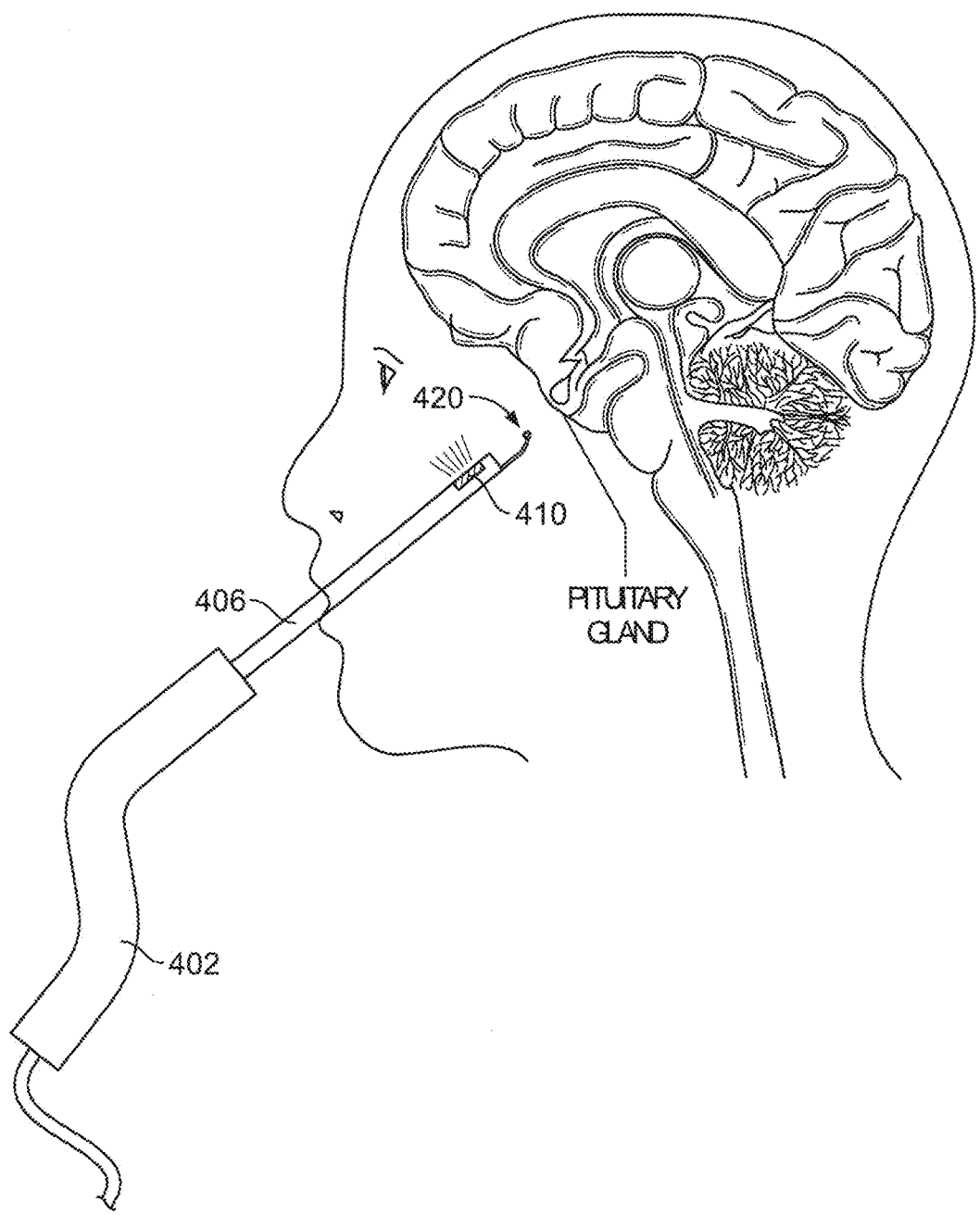
FIG. 14 is a schematic depiction of the exemplary assembly of FIG. 12 showing the assembly positioned at a desired anatomical region/location.

In another exemplary embodiment of the present disclosure, ultrasound assembly 400 (FIG. 12) generally includes a handle member 402 and an elongated probe 406 that is adapted to mount with respect to (or otherwise cooperate with) the handle member 402 (e.g., by way of a bayonet locking mechanism). The elongated probe 406 includes an ultrasound transducer 410 positioned at or near a distal end 412 thereof. The ultrasound transducer 410 may be directed in a perpendicular/substantially perpendicular orientation or an axial/substantially axial orientation relative to the axis of the elongated probe 406. The elongated probe 406 further includes an integrated or modular/interchangeable/detachable device 420 (e.g., an integrated or detachable surgical device such as curette 420) positioned at or near and extending from a distal end 412 thereof.

The exemplary device 420 (e.g., curette 420) generally defines a tissue cutting element 422 which can be used, for example, to resect tissue (e.g., a tumor). The handle member 402 of ultrasound assembly 400 generally cooperates with conventional cabling 414 for communication to and with the elongated probe 406 and, in particular, the distally-positioned ultrasound transducer 410.

Although the illustrated embodiment features a device 420 that takes the form of a curette 420, the present disclosure is not limited thereby. For example, the elongated probe 406 may advantageously interact with one or more integrated and/or modular/detachable accessory items/devices 420 positioned at or near and extending from a distal end 412 thereof. The integrated or modular/detachable items/devices 420 that may be associated with the disclosed elongated probe include, for example, such items/surgical devices 420 as a curette, a probe, a knife, a suction device, a scissor, a cautery unit, forceps, a grasping device and the like.

In use, the elongated probe 406 may be advantageously introduced to a desired anatomical region with real-time ultrasound imaging (e.g., to localize the pituitary gland and surrounding structures). The curette 420 with tissue cutting element 422 may be used to resect tissue (e.g., to remove pituitary tumors while observing the extent of resection through ultrasound imaging). Alternatively, the elongated probe 406 may support alternative structures/elements/surgical devices 420 (e.g., a probe, a knife, a suction device, a scissor, a cautery unit, forceps or a grasping device) that may be used to achieve desired clinical/diagnostic results. The disclosed ultrasound assembly 400 may also be used to explore for residual tumor and visualize cavernous sinus contents (e.g., using color and power Doppler functionalities).

In other embodiments and as shown in FIGS. 18-23 and 29, an exemplary detachable device 20 in accordance with the present disclosure is shown. Detachable surgical device 20 may be similar to device 420 discussed above, with some differences.

In general, detachable device 20 is configured to detachably/releasably mount with respect to various elongated probes (e.g., 106, 256, 356, 406, etc.) and/or ultrasound assemblies (e.g., 100, 250, 350, 400, etc.). More particularly, exemplary detachable surgical device 20 is configured to detachably/releasably mount with respect to the outer periphery of the distal end (e.g., 112, 262, 362, 412) of various elongated probes (e.g., 106, 256, 356, 406, etc.) of the disclosed ultrasound assemblies (e.g., 100, 250, 350, 400, etc.). For example, device 20 can be configured and dimensioned to detachably/releasably mount with respect to the outer periphery 113 of the distal end 112 of elongated probe 106 of ultrasound assembly 100, as similarly shown in FIG. 31 with detachable device 220 (the device 220 is discussed further below).

In general, device 20 includes a housing section 22 and a protruding section 24 that extends or protrudes from the housing section 22. In exemplary embodiments, the housing section 22 is a hollow, substantially cylindrical housing section 22, and defines a lumen or cavity 25 therethrough and/or therein. In general, lumen 25 of housing section 22 is configured and dimensioned to house the outer periphery 113 of the distal end 112 of elongated probe 106 therewithin, as similarly shown in FIG. 31 with detachable device 220. It is also noted again that device 20 could be similarly mounted with respect to the various other elongated probes (e.g., 256, 356, 406, etc.) disclosed herein.

Exemplary housing section 22 includes one or more window members 26 therethrough, with each window member 26 extending through the housing section 22 to expose the lumen 25. In exemplary embodiments, housing section 22 includes two window members 26 and 26A therethrough, with the window members 26, 26A spaced apart from one another on housing section 22. In some embodiments and as shown in FIGS. 19-20, the two window members 26, 26A of housing section 22 are spaced apart or positioned about 180 degrees from each other on housing section 22. Stated another way, exemplary window members 26, 26A are spaced equidistantly apart from one another on housing section 22, although the present disclosure is not limited thereto.

However, it is noted that window members 26, 26A can be spaced apart from one another on housing section 22 a variety of different distances. It is also noted that housing section 22 can include a variety of suitable numbers of window members 26 (e.g., three, four, a plurality, etc.), with each window member 26 spaced apart from one another a variety of different distances. For example, housing section 22 can include three window members 26 (e.g., with each window member 26 spaced equidistantly apart from one another on housing section 22; or spaced apart from one another at other suitable distances).

In some embodiments, window members 26 and 26A are substantially mirror-images of one another, meaning that they expose or define substantially the same area of viewing/imaging through window members 26, 26A. In other embodiments, window members 26, 26A can expose or define different areas of viewing/imaging relative to one another.

Figure 31:
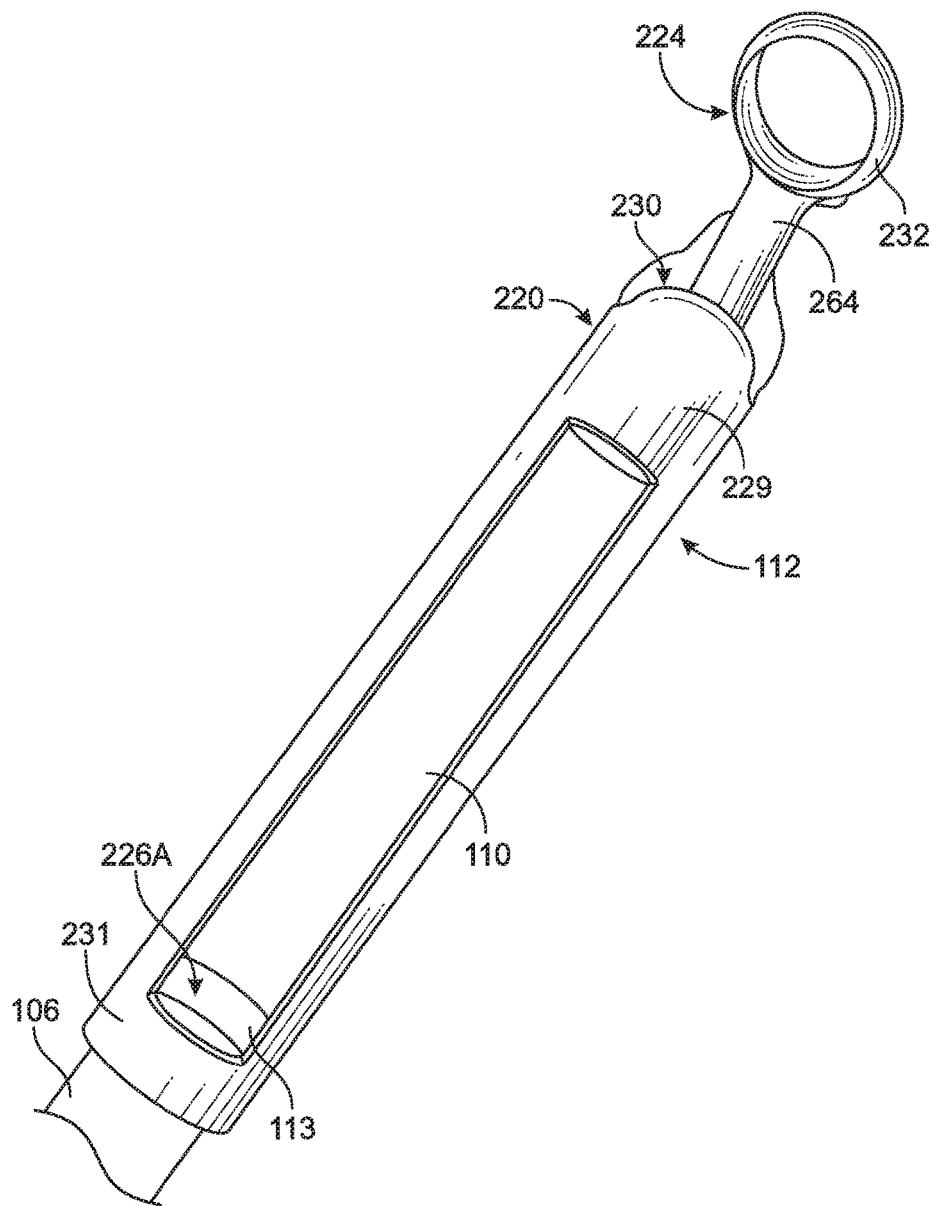
FIG. 31 is a partial top perspective view of the device of FIG. 30, the device detachably mounted with respect to an elongated probe of an ultrasound assembly.

In exemplary embodiments, each window member 26, 26A is configured and dimensioned to substantially expose ultrasound transducer 110 (or the other transducers 260, 360, 410, etc.) when positioned above the ultrasound transducer 110, as similarly shown in FIG. 31 with detachable device 220 and its associated window member 226 exposing ultrasound transducer 110. Thus, exposed ultrasound transducer 110 via window 26 positioned above it (or transducer 110 via window 226 above it, etc.) is available for substantially unobstructed ultrasound imaging through window member 26 when the device 20 is releasably/detachably mounted with respect to the distal end 112 of elongated probe 106.

Moreover and as discussed further below, after device 20 is releasably/detachably mounted with respect to the distal end 112 of elongated probe 106 so that window member 26 is positioned above transducer 110, a user can then circumferentially rotate the device 20 relative to the probe 106 (e.g., about 180 degrees) until the second window member 26A is positioned above transducer 110 for substantially unobstructed ultrasound imaging through window member 26A. As such and as discussed below, device 20 with window members 26, 26A allows a user to utilize the protruding section 24 at two different angles relative to exposed transducer 110 having unobstructed imaging through window member 26 or window member 26A.

Exemplary window members 26, 26A each extend from a distal end 27 to a proximal end 28 on housing section 22 (FIG. 19). The distal end 21 of housing section 22 includes a distal annular or ring-like section 29, and the proximal end 23 of housing section 22 includes a proximal annular or ring-like section 31.

In exemplary embodiments, annular sections 29, 31 are substantially continuous, and window members 26, 26A do not extend through annular sections 29, 31, although the present disclosure is not limited thereto. For example, it is noted that window members 26 and/or 26A can extend through annular section 29, and/or window members 26 and/or 26A can extend through annular section 31.

In general, annular sections 29, 31 are configured and dimensioned to surround and/or house the outer periphery 113 of the distal end 112 of elongated probe 106, as similarly shown in FIG. 31 with detachable device 220 and annular sections 229, 231 (or surround the other probes disclosed herein). In certain embodiments, housing section 22 (e.g., section 29 and/or 31) can include a recess or the like (e.g., a small recess integrated on the interior surface of housing 22) that is configured and dimensioned to engage a tab or protrusion on the outer periphery 113 of the distal end 112 of elongated probe 106. In other embodiments, the outer periphery 113 includes a recess or the like that is configured to engage a tab or protrusion on the interior surface of housing 22.

In some embodiments and as shown in FIG. 20, the distal end 21 of housing section 22 includes an abutment surface 30 that is configured and dimensioned to abut against the distal end 112 of probe 106 when device 20 is mounted with respect to probe 106, as similarly shown in FIG. 31 with detachable device 220 and abutment surface 230. Abutment surface 30 may or may not extend across the distal end 21 of housing section 22 to prevent lumen 25 from extending through distal end 21 of housing section 22.

As noted above and as shown in FIGS. 18 and 20, protruding section 24 extends or protrudes from housing section 22. In general, protruding section 24 extends or protrudes from the distal end 21 of housing 22. Protruding section 24 may or may not be integral with housing section 22.

In some embodiments, exemplary protruding section 24 takes the form of a curette member 24 or the like, although the present disclosure is not limited thereto. Curette member 24 generally defines a tissue cutting element 32 which can be used, for example, to resect tissue (e.g., a tumor).

However, rather than or in addition to tissue cutting element 32, protruding section 24 can take a variety of different forms/shapes/geometries, and/or include a variety of different instruments/devices and/or combination of instruments/devices. It is noted that although the illustrated embodiment features a device 20 that includes a protruding section 24 having a tissue cutting element 32, the present disclosure is not limited thereby. For example, other instruments/elements/features that may be associated with the disclosed protruding section 24 include, without limitation, a probe, a knife, a suction device, a scissor, a cautery unit, forceps, a grasping device and the like. It is noted that such other instruments/elements/features may be associated with protruding section 24 in addition to or in lieu of tissue cutting element 32.

In exemplary embodiments and as shown in FIGS. 18 and 20, the tissue cutting element 32 of protruding section 24 extends from the housing section 22 at about a 45 degree angle relative to the longitudinal axis B of lumen 25, although the present disclosure is not limited thereto. Rather, tissue cutting element 32 of protruding section 24 can extend from the housing section 22 at other angles relative to the longitudinal axis B of lumen 25 (e.g., at about a 90 degree angle, as similarly discussed below with reference to element 132 of device 120).

In use, it is noted that device 20 can be detachably/releasably mounted with respect to the outer periphery 113 of the distal end 112 of elongated probe 106 of ultrasound assembly 100, as similarly shown in FIG. 31 with detachable device 220 (or mounted to the distal end (e.g., 262, 362, 412) of other various elongated probes (e.g., 256, 356, 406, etc.) of the disclosed ultrasound assemblies (e.g., 250, 350, 400, etc.)).

More particularly, a user could position the distal end 112 of probe 106 into the lumen 25 of the proximal end 23 of housing section 22, and thereafter advance the distal end 112 within the lumen 25 of housing section 22 until the distal end 112 of probe 106 contacts and/or is positioned adjacent to or near the abutment surface 30 of the distal end 21 of housing section 22 (as similarly shown in FIG. 31 with detachable device 220).

In this position, the outer periphery 113 of the distal end 112 of elongated probe 106 is positioned or housed within the lumen 25 of the housing section 22, with the annular sections 29, 31 surrounding and/or housing the outer periphery 113 of the distal end 112 of elongated probe 106, and with the distal end 112 of probe 106 contacting and/or positioned adjacent to or near the abutment surface 30 of the distal end 21 of housing section 22. As such, exemplary device 20 advantageously fits snuggly on the distal end 112 of probe 106 so that it will not move on its own once it is positioned on the probe 106, but allows a user to remove the device 20 from the probe 106 when desired, and also allows the user to rotate the device 20 circumferentially around the probe 106 (e.g., device 20 can be moved/rotated circumferentially around the circumference of probe 106) when desired, as further discussed below.

For example, after the distal end 112 of probe 106 is housed within lumen 25 of the housing section 22 (e.g., with the annular sections 29, 31 surrounding the distal end 112), a user could rotate the device 20 circumferentially around the probe 106 until window member 26 is positioned above transducer 110 for substantially unobstructed ultrasound imaging through window member 26.

In use, the probe 106 and detachably mounted device 20 may be advantageously introduced to a desired anatomical region with real-time ultrasound imaging via transducer 110 operating through window member 26 (e.g., to localize the pituitary gland and surrounding structures). The protruding section 24 with tissue cutting element 32 may be used to resect tissue (e.g., to remove pituitary tumors while observing the extent of resection through ultrasound imaging). Alternatively, the mounted device 20 may support alternative structures/elements/surgical devices/sections 24 (e.g., a probe, a knife, a suction device, a scissor, a cautery unit, forceps or a grasping device) that may be used to achieve desired clinical/diagnostic results.

Thereafter, a user can then rotate the device 20 circumferentially around and relative to the probe 106 (e.g., about 180 degrees) until the second window member 26A is positioned above transducer 110 for substantially unobstructed ultrasound imaging through window member 26A.

In this position, the probe 106 and detachably mounted device 20 may be advantageously introduced to a desired anatomical region with real-time ultrasound imaging via transducer 110 operating through window member 26A, and the protruding section 24 with tissue cutting element 32 may be used to resect tissue. As such and as noted, device 20 with window members 26, 26A allows a user to utilize the protruding section 24 at two different angles relative to exposed transducer 110 having unobstructed imaging through window member 26 or window member 26A.

More specifically, when the transducer 110 is aligned with window 26, the protruding section 24 and tissue cutting element 32 is positioned about 180 degrees around the probe 106 from transducer 110 (e.g., the transducer 110 is positioned on the top side of the probe 106, while the cutting element 32 is positioned on the bottom side of the probe). Thus, imaging can occur via transducer 110 through window 26 at the top side of the probe 106, and cutting can occur via element 32 at the bottom side of the probe.

After transducer 110 is aligned with window 26A, the protruding section 24 and tissue cutting element 32 is positioned on the same side of the probe 106 as the transducer 110 (e.g., the transducer 110 is positioned on the top side of the probe 106, and the cutting element 32 is positioned on the top side of the probe). Thus, imaging can occur via transducer 110 through window 26A at the top side of the probe 106, and cutting can occur via element 32 at the top side of the probe.

When desired by a user, the device 20 can be removed from probe 106. More particularly, a user can hold the probe 106 or handle 102 in one hand, and slide the device 20 off of and away from the distal end 112 of the probe 106 with the other hand.

FIGS. 24-28 depict an alternative detachable device 120 that is similar to device 20, with some differences. Similar to device 20, the device 120 is configured to detachably/releasably mount with respect to various elongated probes (e.g., 106, 256, 356, 406, etc.). Device 120 includes a housing section 122 and a protruding section 124 that extends or protrudes from the housing section 122. Housing section 122 is a hollow, substantially cylindrical housing section 122 having a lumen or cavity 125 therethrough. Housing section 122 includes two window members 126 and 126A therethrough, with each window member 126, 126A configured to substantially expose ultrasound transducer 110 when positioned above the ultrasound transducer 110. Thus, exposed ultrasound transducer 110 via window 126 positioned above it (or transducer 110 via window 126A above it) is available for substantially unobstructed ultrasound imaging through window member 126 when the device 120 is releasably/detachably mounted with respect to the distal end 112 of elongated probe 106.

The distal end 121 of housing section 122 includes an abutment surface 130 that is configured and dimensioned to abut against the distal 112 of probe 106 when device 120 is mounted with respect to probe 106.

As shown in FIGS. 24 and 26, protruding section 124 extends or protrudes from housing section 122. In exemplary embodiments, the tissue cutting element 132 of protruding section 124 extends from the housing section 122 at about a 90 degree angle relative to the longitudinal axis B' of lumen 125, although the present disclosure is not limited thereto.

Device 120 can be detachably mounted to and removed from probe 106, as similarly discussed above in conjunction with device 20. Moreover, after the device 120 is mounted to probe 106, the device 120 can be circumferentially rotated around and relative to probe 106 so that window 126 or 126A is aligned with transducer 110. As such and as similar to device 20, the device 120 can be mounted to probe 106 by sliding the device 120 down the distal end 112 and lining up one of the two windows 126, 126A with the transducer 110. The device 120 can then be turned while still on the probe 106 to the other window 126 or 126A, thus giving the user a different cutting angle with cutting element 132.

Figure 30:
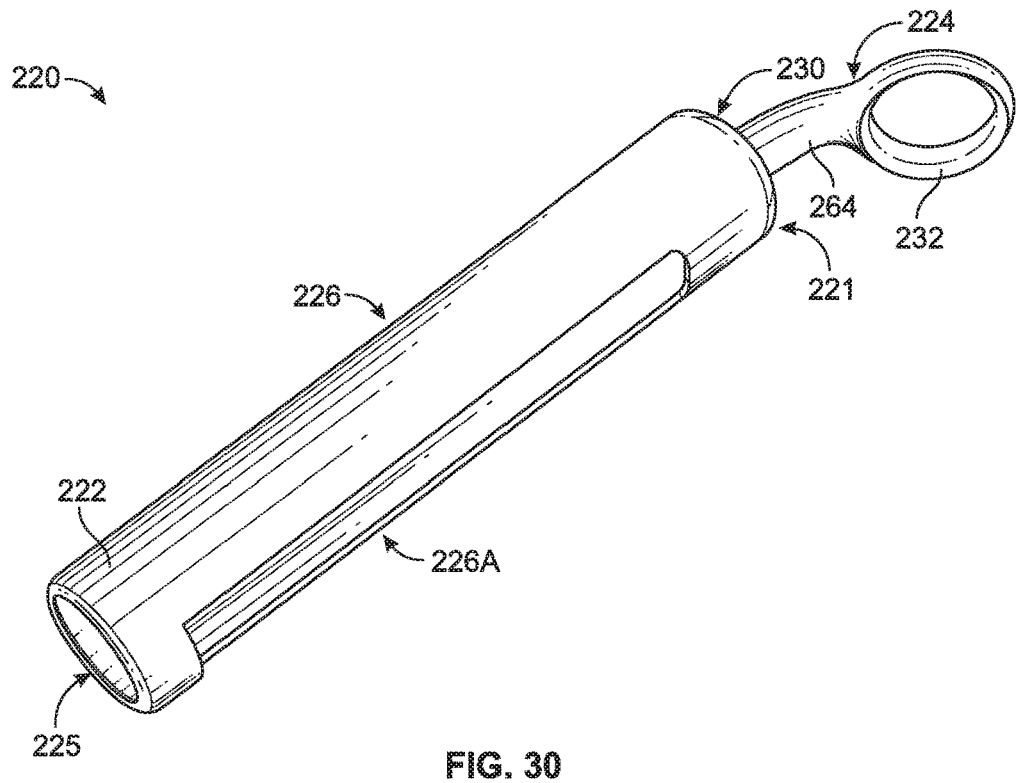
FIG. 30 is a side perspective view of another exemplary detachable device configured to mount with respect to various elongated probes and/or ultrasound assemblies.

FIGS. 30-31 depict another alternative detachable device 220 that is similar to device 20, 120 with some differences.

Similar to device 20/120, the device 220 is configured to detachably/releasably mount with respect to various elongated probes (e.g., 106, 256, 356, 406, etc.). Device 220 includes a housing section 222 and a protruding section 224 that extends or protrudes from the housing section 222. Housing section 222 is a hollow, substantially cylindrical housing section 222 having a lumen or cavity 225 therethrough. Housing section 222 includes two window members 226 and 226A therethrough, with each window member 226, 226A configured to substantially expose ultrasound transducer 110 when positioned above the ultrasound transducer 110. Thus, exposed ultrasound transducer 110 via window 226 positioned above it (or transducer 110 via window 226A above it) is available for substantially unobstructed ultrasound imaging through window member 226 when the device 220 is releasably/detachably mounted with respect to the distal end 112 of elongated probe 106.

The distal end 221 of housing section 222 includes an abutment surface 230 that is configured and dimensioned to abut against the distal 112 of probe 106 when device 220 is mounted with respect to probe 106.

As shown in FIGS. 30-31, protruding section 224 extends or protrudes from housing section 222. In exemplary embodiments, the tissue cutting element 232 (or other alternative surgical device/element/feature) of protruding section 224 extends from an extending member 264 of protruding section 224.

Device 220 can be detachably mounted to and removed from probe 106, as similarly discussed above in conjunction with device 20/120. Moreover, after the device 220 is mounted to probe 106, the device 220 can be circumferentially rotated around and relative to probe 106 so that window 226 or 226A is aligned with transducer 110. As such and as similar to device 20/120, the device 220 can be mounted to probe 106 by sliding the device 220 down the distal end 112 and lining up one of the two windows 226, 226A with the transducer 110. The device 220 can then be turned while still on the probe 106 to the other window 226 or 226A, thus giving the user a different cutting angle with cutting element 232.

According to the present disclosure, the disclosed instruments/assemblies (e.g., 100, 250, 350, 400, etc.) and associated devices (e.g., 20, 120, 220, 420—when present) may be used in conjunction with an endoscope and/or endoscopic camera, thereby permitting simultaneous ultrasound imaging and conventional viewing. Thus, the elongated probe/member (e.g., 106, 256, 356, 406, etc.) may be adapted to cooperate with an endoscopic element that transmits images for viewing by medical personnel, thereby augmenting the ultrasound imaging delivered by the ultrasound transducer (e.g., 110, 260, 360, 410) associated with the elongated probe/member. In addition, the disclosed elongated probe/member may include one or more fiducials (e.g., flats or notches) or other antennae that may allow for the handle member and/or elongated member to be monitored/viewed by conventional neuro-navigation systems. In this way, the disclosed assemblies/systems (e.g., 100, 250, 350, 400, etc.) may be advantageously integrated into intra-operative navigation systems, such as brain lab or stealth systems, so that the disclosed device/assembly may serve as a pointer for intra-operative navigation systems while also giving real-time feedback using ultrasound, which optionally may be merged with pre-operative MRI or CT scans.

Although the systems, assemblies and methods have been described with respect to exemplary embodiments herein, it is apparent that modifications, variations, changes and/or enhancements may be made thereto without departing from the scope of the disclosure as defined by the appended claims. For example, as an alternative to the use of a side-firing ultrasound transducer as described hereinabove, and/or in addition thereto, one or more end-firing ultrasound transducers, and/or 360 degree ultrasound transducers may be employed, whether mounted with respect to the distal end of the longitudinal shaft of the associated ultrasound probe, adjacent thereto, or otherwise, for use as desired by the surgical practitioner. Accordingly, the present disclosure expressly encompasses all such modifications, variations, changes and/or enhancements. Moreover, the assemblies, systems and methods of the present disclosure are susceptible to many implementations and applications, as will be readily apparent to persons skilled in the art from the disclosure hereof.

Whereas the disclosure has been described in connection with ultrasound assemblies for cranial procedures/applications, such description has been utilized only for purposes of disclosure and is not intended as limiting the disclosure. To the contrary, it is to be recognized that the disclosed ultrasound assemblies (e.g., 100, 250, 350, 400, etc.) and related instruments/devices are capable of use for other procedures/applications (e.g., spinal surgical procedures, orthopedic applications, minimally invasive surgical procedures, etc., as described and disclosed in U.S. Pat. Nos. 8,343,056 and 8,206,306, the entire contents of each being incorporated by reference herein).

For example, exemplary devices 20, 120, 220, 420, etc. of the present disclosure can be mounted with respect to the medical diagnostic instruments (e.g., to the distal ends of the longitudinal shafts of the ultrasound probes of the medical diagnostic instruments) that are described and disclosed in U.S. Pat. Nos. 8,343,056 and 8,206,306 noted above, and thereafter utilized for surgical/clinical/diagnostic purposes (e.g., during a broad variety of spinal surgical applications/procedures or the like).

Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. An ultrasound assembly comprising:
   an elongated probe extending from a proximal end to a distal end, the proximal end extending from and mounted with respect to a handle member, the elongated probe supporting an ultrasound transducer configured to obtain ultrasound images to determine a location of the elongated probe relative to surrounding anatomical structures or features, the ultrasound transducer including an array of ultrasonic energy generation elements; and a detachable surgical device positioned proximal to and detachably mounted to an outer periphery of the distal end of the elongated probe, the detachable surgical device including a housing section and a protruding section that extends from a distal end of the housing section, the housing section having: (i) a first window member configured to align with and expose the ultrasound transducer through the first window member when the detachable surgical device is in a first mounted position relative to the elongated probe, and (ii) a second window member configured to align with and expose the ultrasound transducer through the second window member when the detachable surgical device is in a second mounted position relative to the elongated probe;

wherein the elongated probe, ultrasound transducer and detachable surgical device are cooperatively configured, oriented and dimensioned to allow an operator to insert the detachable surgical device and the distal end of the elongated probe into a desired anatomical location to permit the operator to: (i) perform thereat a surgical procedure of the desired anatomical location by utilizing the detachable surgical device mounted to the outer periphery of the distal end of the elongated probe, and (ii) obtain ultrasound imaging of the desired anatomical location via the exposed ultrasound transducer when the detachable surgical device is in the first or second mounted position relative to the elongated probe;

wherein when the detachable surgical device is in the first mounted position relative to the elongated probe to align with and expose the ultrasound transducer through the first window member, this thereby allows the operator to utilize the protruding section at a first angle relative to the exposed ultrasound transducer through the first window member; and wherein when the detachable surgical device is in the second mounted position relative to the elongated probe to align with and expose the ultrasound transducer through the second window member, this thereby allows the operator to utilize the protruding section at a second angle relative to the exposed ultrasound transducer through the second window member.

2. The ultrasound assembly of claim 1, wherein the protruding section includes a curette member having a tissue cutting element; and
wherein the first angle of the utilized protruding section is different than the second angle of the utilized protruding section.

3. The ultrasound assembly of claim 2, wherein the tissue cutting element of the protruding section extends from the housing section at from about a 45 degree angle to about a 90 degree angle relative to a longitudinal axis of the housing section.

4. The ultrasound assembly of claim 1,
wherein the protruding section includes an instrument selected from a group consisting of a curette, a probe, a knife, a suction device, a scissor, a cautery unit, forceps and a grasping device.

5. The ultrasound assembly of claim 1, wherein the housing section of the detachable surgical device is hollow and substantially cylindrical, and defines a lumen within the housing section; and
wherein the first and second window members each extend through the housing section to expose the lumen of the housing section.

6. The ultrasound assembly of claim 5, wherein the lumen is configured and dimensioned to house the outer periphery of the distal end of the elongated probe.

7. The ultrasound assembly of claim 5, wherein the first and second window members each extend from a distal end to a proximal end on the cylindrical housing section.

8. The ultrasound assembly of claim 5, wherein the first and second window members are spaced about 180 degrees from each other on the cylindrical housing section.

9. The ultrasound assembly of claim 8, wherein after the detachable surgical device is detachably mounted to the distal end of the elongated probe so that first window member is positioned above the ultrasound transducer in the first mounted position relative to the elongated probe for substantially unobstructed ultrasound imaging through the first window member, a user can then circumferentially rotate the detachable surgical device about 180 degrees around the probe until the second window member is positioned above the ultrasound transducer in the second mounted position relative to the elongated probe for substantially unobstructed ultrasound imaging through the second window member.

10. The ultrasound assembly of claim 1, wherein the first and second window members are spaced equidistantly apart from one another on the housing section.

11. The ultrasound assembly of claim 1, wherein after the detachable surgical device is detachably mounted to the distal end of the elongated probe so that first window member is positioned above the ultrasound transducer in the first mounted position relative to the elongated probe for substantially unobstructed ultrasound imaging through the first window member, a user can then circumferentially rotate the detachable surgical device around the probe until the second window member is positioned above the ultrasound transducer in the second mounted position relative to the elongated probe for substantially unobstructed ultrasound imaging through the second window member.

12. The ultrasound assembly of claim 1, wherein a distal end of the housing section includes a distal annular section, and a proximal end of the housing section includes a proximal annular section; and
wherein the distal and proximal annular sections are configured and dimensioned to surround and house the outer periphery of the distal end of the elongated probe.

13. The ultrasound assembly of claim 1, wherein a distal end of the housing section includes an abutment surface that is configured and dimensioned to abut against the distal end of the elongated probe.

14. The ultrasound assembly of claim 1, wherein the first and second window members are substantially mirror images of one another, thereby exposing substantially the same area of imaging through the first and second window members.

15. The ultrasound assembly of claim 1 further comprising at least one hollow receiver member mounted with respect to the elongated probe;
wherein the at least one hollow receiver member is configured and dimensioned to receive a K-wire or guidewire.

16. The ultrasound assembly of claim 15, wherein the at least one hollow receiver member includes a first hollow receiver member and a second hollow receiver member mounted with respect to the elongated probe, each hollow receiver member configured and dimensioned to receive the K-wire or guidewire; and
wherein the first hollow receiver member is mounted with respect to a distal portion of the elongated probe and the second hollow receiver member is mounted with respect to a proximal end of the elongated probe.

17. An ultrasound assembly comprising:
an elongated probe extending from a proximal end to a distal end, the proximal end extending from and mounted with respect to a handle member, the elongated probe supporting an ultrasound transducer configured to obtain ultrasound images to determine a location of the elongated probe relative to surrounding anatomical structures or features, the ultrasound transducer including an array of ultrasonic energy generation elements; and
a detachable surgical device positioned proximal to and detachably mounted to an outer periphery of the distal end of the elongated probe, the detachable surgical device including a housing section and a protruding section that extends from a distal end of the housing section, the housing section having: (i) a first window member configured to align with and expose the ultrasound transducer when the detachable surgical device is in a first mounted position relative to the elongated probe, and (ii) a second window member configured to align with and expose the ultrasound transducer when the detachable surgical device is in a second mounted position relative to the elongated probe;
wherein the elongated probe, ultrasound transducer and detachable surgical device are cooperatively configured, oriented and dimensioned to allow an operator to insert the detachable surgical device and the distal end of the elongated probe into a desired anatomical location to permit the operator to: (i) perform thereat a surgical procedure of the desired anatomical location by utilizing the detachable surgical device mounted to the outer periphery of the distal end of the elongated probe, and (ii) obtain ultrasound imaging of the desired anatomical location via the exposed ultrasound transducer when the detachable surgical device is in the first or second mounted position relative to the elongated probe;
wherein when the detachable surgical device is in the first mounted position relative to the elongated probe to align with and expose the ultrasound transducer through the first window member, this thereby allows the operator to utilize the protruding section at a first angle relative to the exposed ultrasound transducer through the first window member;
wherein when the detachable surgical device is in the second mounted position relative to the elongated probe to align with and expose the ultrasound transducer through the second window member, this thereby allows the operator to utilize the protruding section at a second angle relative to the exposed ultrasound transducer through the second window member;
wherein the first angle of the utilized protruding section is different than the second angle of the utilized protruding section;
wherein the protruding section includes a curette member having a tissue cutting element;
wherein the housing section of the detachable surgical device is hollow and substantially cylindrical, and defines a lumen within the housing section;
wherein the first and second window members each extend through the housing section to expose the lumen of the housing section;
wherein the first and second window members are spaced about 180 degrees from each other on the cylindrical housing section;
wherein after the detachable surgical device is detachably mounted to the distal end of the elongated probe so that first window member is positioned above the ultrasound transducer in the first mounted position relative to the elongated probe for substantially unobstructed ultrasound imaging through the first window member, a user can then circumferentially rotate the detachable surgical device about 180 degrees around the probe until the second window member is positioned above the ultrasound transducer in the second mounted position relative to the elongated probe for substantially unobstructed ultrasound imaging through the second window member;
wherein the first and second window members each extend from a distal end to a proximal end on the cylindrical housing section; and
wherein the tissue cutting element of the protruding section extends from the housing section at from about a 45 degree angle to about a 90 degree angle relative to a longitudinal axis of the lumen of the housing section.

18. The ultrasound assembly of claim 17, wherein the first and second window members are substantially mirror images of one another, thereby exposing substantially the same area of imaging through the first and second window members.

19. The ultrasound assembly of claim 17,
wherein the lumen is configured and dimensioned to house the outer periphery of the distal end of the elongated probe.

20. The ultrasound assembly of claim 17, wherein the distal end of the housing section includes a distal annular section, and a proximal end of the housing section includes a proximal annular section;
wherein the distal and proximal annular sections are configured and dimensioned to surround and house the outer periphery of the distal end of the elongated probe; and
wherein the distal end of the housing section includes an abutment surface that is configured and dimensioned to abut against the distal end of the elongated probe.

* * * * *